United States Patent [19]

Thorne et al.

[11] Patent Number: 5,549,708

[45] Date of Patent: Aug. 27, 1996

[54] SELF RETRACTING MEDICAL NEEDLE APPARATUS AND METHODS

[75] Inventors: Gale H. Thorne, Bountiful; David L. Thorne, Kaysville; Sandra A. Thorne, West Jordan, all of Utah

[73] Assignee: Specialized Health Products, Inc., Bountiful, Utah

[21] Appl. No.: 455,514

[22] Filed: May 31, 1995

Related U.S. Application Data

[63] Continuation of Ser. No. 370,728, Jan. 10, 1995, Pat. No. 5,480,385.

[51] Int. Cl.⁶ ........................................... A61M 5/00
[52] U.S. Cl. ........................ 604/110; 604/192; 128/763
[58] Field of Search .................................. 604/110, 187, 604/192, 198, 263; 128/763–765, 919

[56] References Cited

U.S. PATENT DOCUMENTS

| | | | |
|---|---|---|---|
| 4,676,783 | 6/1987 | Jagger | 604/171 |
| 4,813,936 | 3/1989 | Schroeder | 604/195 |
| 4,850,374 | 7/1989 | Diaz-Ramos | 128/763 |
| 4,892,525 | 1/1990 | Hermann, Jr. | 604/263 |
| 4,909,794 | 3/1990 | Haber | 604/195 |
| 4,946,446 | 8/1990 | Vadher | 604/198 |
| 4,955,870 | 9/1990 | Ridderheim | 604/195 |
| 4,966,593 | 10/1990 | Lennox | 604/198 |
| 4,978,340 | 12/1990 | Terrill | 604/195 |
| 4,985,021 | 1/1991 | Straw | 604/198 |
| 4,986,816 | 1/1991 | Steiner | 604/192 |
| 4,988,339 | 1/1991 | Vadher | 604/197 |
| 4,994,034 | 2/1991 | Botich | 604/110 |
| 4,995,870 | 2/1991 | Baskas | 604/110 |
| 5,092,853 | 3/1992 | Couvertier | 604/195 |
| 5,098,402 | 3/1992 | Davis | 604/195 |
| 5,114,404 | 5/1992 | Paxton | 604/110 |
| 5,147,303 | 9/1992 | Martin | 604/110 |
| 5,180,370 | 1/1993 | Gillespie | 604/110 |
| 5,188,599 | 2/1993 | Botich | 604/110 |
| 5,193,552 | 3/1993 | Columbus et al. | 128/768 |
| 5,195,983 | 3/1993 | Boese | 604/192 |
| 5,195,985 | 3/1993 | Hall | 604/195 |
| 5,205,823 | 4/1993 | Zdeb | 604/110 |
| 5,205,824 | 4/1993 | Mazur | 604/110 |
| 5,209,739 | 5/1993 | Talsay | 604/195 |
| 5,215,533 | 6/1993 | Robb | 604/195 |

(List continued on next page.)

OTHER PUBLICATIONS

Patricia Seremet, "Small Tolland Company Takes Jab at Safety Needle Market," *The Hartford Courant*, Sep. 13, 1994, pp. F1 and F3.

*Primary Examiner*—John D. Yasko
*Attorney, Agent, or Firm*—Gale H. Thorne

[57] ABSTRACT

Method and apparatus associated with safe retraction of medical needles after use. Embodiments are disclosed for self-retracting needle systems for both blood withdrawal and catheter insertion systems. Two blood withdrawal embodiments are disclosed. Invention manufacture requires only a minimal number and complexity of parts such that a projected manufacturing cost is potentially low enough to permit the apparatus to be cost competitive with contemporary non-self retracting needle systems. Methods for making and assembling each of the disclosed the embodiments is also disclosed. One of the blood withdrawal embodiments can be made with as few as three molded parts. Energy storing retracting mechanisms comprise elastic tubing and vacuum generating piston parts. Triggerable release mechanisms generally comprise two parts or two segments of one part molded about a medical needle. Each release mechanism involves one part or segment which is securely affixed to the needle and one part or segment which is free to slide and rotate about the needle. The blood withdrawal embodiment effectively inhibits regurgitant flow from the needle. The catheter insertion embodiment captures blood effluent from the catheter upon retraction of the needle. In all embodiments, needle retraction is a single handed operation permitting a technicians other hand to be used in wound care. Use of frangible parts permits the apparatus housing to be hermetically sealed and used as a transport container to further reduce apparatus costs.

21 Claims, 18 Drawing Sheets

U.S. PATENT DOCUMENTS

| | | | |
|---|---|---|---|
| 5,246,428 | 9/1993 | Falknor | 604/198 |
| 5,254,099 | 10/1993 | Kuracina | 604/198 |
| 5,256,153 | 10/1993 | Hake | 604/198 |
| 5,267,976 | 12/1993 | Guerineau | 604/198 |
| 5,320,606 | 6/1994 | Jore | 604/110 |
| 5,356,392 | 10/1994 | Firth | 604/198 |
| 5,374,250 | 12/1994 | Dixon | 604/110 |
| 5,403,286 | 4/1995 | Lockwood, Jr. | 604/110 |

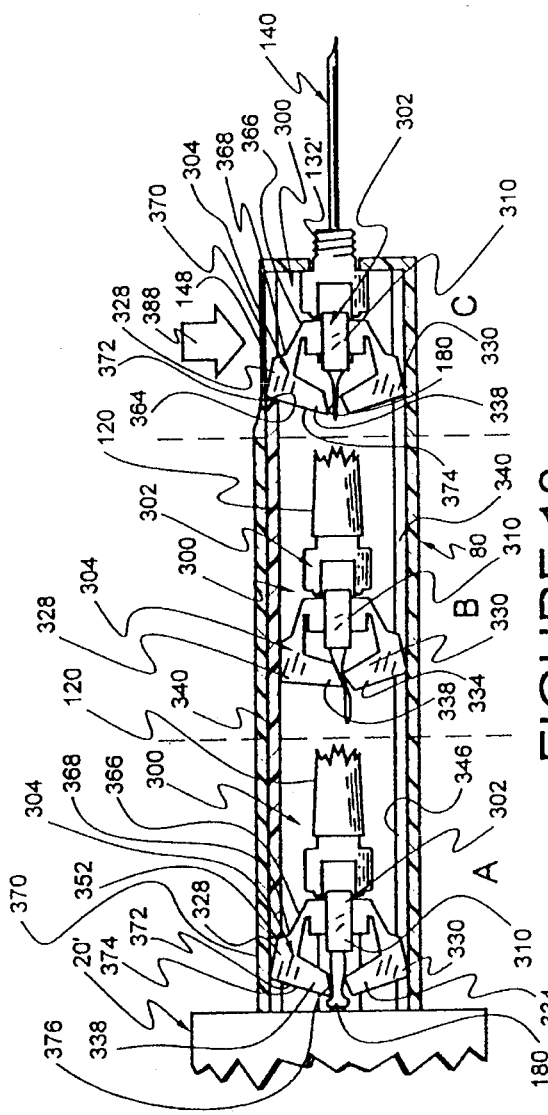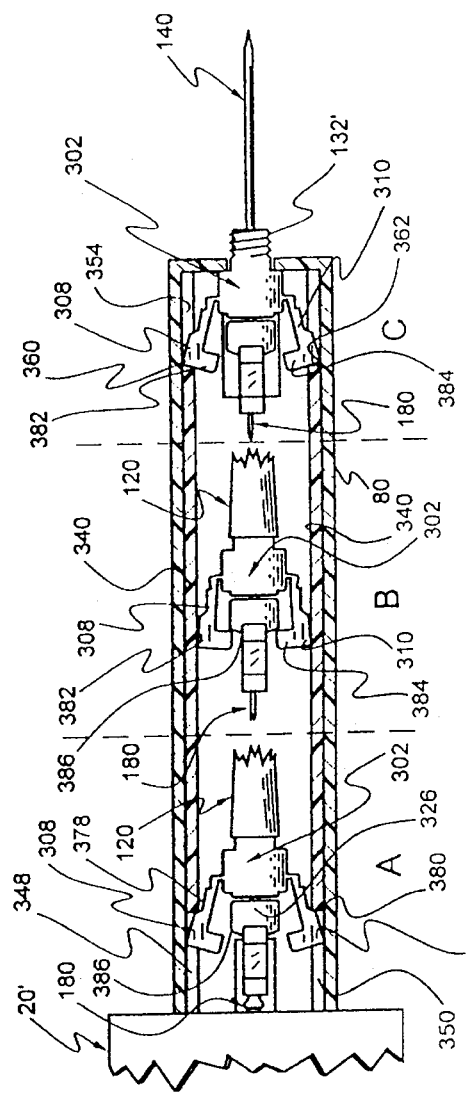

SELF RETRACTING MEDICAL NEEDLE APPARATUS AND METHODS

CONTINUITY

This application is a Continuation of U.S. patent application Ser. No. 08/370,728 filed Jan. 10, 1995 and now U.S. Pat. No. 5,480,385.

FIELD OF INVENTION

This invention relates generally to medical needle apparatus and methods and particularly to apparatus comprising medical needles which are self-retracting from an extended position at which the needle is used to a retracted position where the needle is fully withdrawn to be encased within a housing for safe disposal. Further, the invention is related to medical products which may only be used once to eliminate cross contamination from one patient to another and to those medical products which have sterile parts inherently protected from contamination without need of additional packaging apparatus.

PRIOR ART

Problems associated with inadvertent needle sticks are well known in the art of blood withdrawal, transdermal medication injection, catheter emplacement and other medical procedures involving uses of medical needles. Ever increasing attention is being paid to needle stick problems due to the contemporary likelihood of being exposed to AIDS and Hepatitis.

Commonly, procedures involving needle withdrawal require a technician to use one hand to place pressure at the wound site where a needle is being withdrawn while removing the needle apparatus with the other hand. It is common practice for the tending technician care to give higher priority to care for the wound than is given to disposal of a needle. Such priority either requires an available sharps container within ready reach or another means for safe disposal without leaving the patient's side. Providing adequate care is often compounded by patient condition and mental state (e.g. in burn units and psychiatric wards). Under such conditions, it is often difficult, if not impossible, to take appropriate procedures to properly dispose of a used, exposed needle while caring for a patient.

Widespread knowledge and history associated with needle care and disposal problems have resulted in conception and disclosure of a large number of devices each of which represents an attempt to provide not only a solution to the problem of needle sticks, but a device which is commercially viable (cost and price competitive with currently used non-self retracting devices). Though some devices describe application in the area of blood withdrawal (see U.S. Pat. Nos. 4,850,374 (Nydia Diaz-ramos) and 5,195,985 (Hall)), most contemporary related art is directed toward syringes and like devices. Broadly, related art may be classified into two categories, devices which operate manually and devices which comprises self-contained needle retraction.

Examples of manually operated medical needle devices are provided in U.S. Pat. Nos. 4,676,783 (Jagger et al.), 4,83,936 (Schroeder), 4,909,794 (Haber), 4,978,340 (Terrill et al.), 4,995,870 (Baskas), 5,098,402 (Davis), 5,180,370 (Gellespie), 5,188,599 (Botich et al.), 5,195,985 (Hall), 5,205,823 (Zdeb), 5,205,824 (Mazur), 5,215,533 (Robb), and 5,256,153 (Hake). Manual withdrawal is generally a two-handed procedure, making wound care a secondary step or requiring an added medical technician.

Examples of self-retracting devices are found in U.S. Pat. Nos. 4,946,446 (Vadher), 4,955,870 (Ridderheim et al.), 4,966,593 (Lennox), 4,988,339 (Vadher), 4,994,034 (Botich et al.), 5,114,404 (Paxton et al.), 5,147,303 (Martin), 5,092,853 (Couvertier), 5,246,428 (Falknor), 5,254,099 (Karacina), and 5,267,976 (Guerineau et al.). Guerineau et al. discloses self-retraction resulting from a vacuum force while others disclosed above generally disclose self-retraction resulting from release of a cocked or biased spring.

Generally, other than acceptance of the type of operation offered by such devices, commercial viability is dependent upon manufacturing cost. Purchase decisions in the area in which these devices are used are very cost sensitive. If gains in either improvement in safety or in labor savings are not found to be sufficiently competitive with contemporary competitive items, the devices are usually not found to be commercially viable. Motivation for providing a cost competitive self-retracting needle apparatus coupled with improved safety of use of the apparatus resulted in conception of the instant invention disclosed herein.

BRIEF SUMMARY AND OBJECTS OF THE INVENTION

In brief summary, this novel invention alleviates known major problems which result from injury-related needle sticks which occur as needle tips are bared at the end of a needle insertion procedure. In a preferred embodiment, operation of the invention involves extension of a covered needle by frangibly separating the needle cover from a housing and pulling the cover and needle from the device for use. The act of pulling the cover and needle from the device energizes a force storing memory element and cocks a releasable latch. The cover is removed from the needle, and needle is used in a medical procedure (e.g. for acquiring a blood sample or for catheter insertion).

Once the procedure is complete, a simple distortion of a portion of the housing, preferably by squeezing the housing by the thumb and forefinger of one hand retracts the needle safely into the housing. It is important to note that the needle can be removed by simple squeezing action of an attending technician's hand, leaving the technician's other hand free for other concurrent medical procedures, such as care of the wound site from which the needle is withdrawn. After withdrawal, the needle is fully inclosed and contained, permitting the needle apparatus to be laid aside without fear of an inadvertent needle stick while full attentive care is provided to the patient.

In a blood sampling embodiment, the invention comprises a housing/transport container, a needle/hub assembly and a barrel/hub component. In preferred embodiments, apparatus of the instant invention require as few as three molded parts, each part being representative of the container, assembly and component mentioned above.

The housing/transport container is preferably molded as a single multi-cylinder part. The part consists of two cylinders, an inner cylinder and an outer cylinder, and a protective flap connected by a living hinge to the outer cylinder. The inner and outer cylinders are mutually closed at one end and open at the other. The inner cylinder forms a needle cover which has an attachment (e.g. a female threaded or bayonet coupling) for joining to a male connection to provide a separable attachment to the needle/hub assembly. The outer cylinder of the housing/transport container is preferably hermetically sealed to the barrel/hub component to form a closed housing which is capable of being used as a transport package which maintains needle sterility until opened at the beginning of a medical procedure.

Though other forming processes may be used, needle/hub assembly is preferably formed as a single part which is injection molded about a medical needle. The assembly comprises the medical needle, (a) a fore-portion of the part more proximal to the sharp end of the needle and disposed about the needle and juxtaposed with a portion of the elongated length of the needle but left by the molding process to move freely upon the needle and (b) an-aft portion which is more distal from the sharp end of the needle and also disposed about the needle but firmly and securely affixed to the needle. The fore-portion comprises the male connection which separably affixes to the needle cover by the connection earlier referenced. The fore-portion also comprises at least one latch which locks to a portion of the container when the needle is pulled forth from the container for use. The act of pulling the needle fully forth to a locked position cocks a needle portion of the needle assembly in position for release and retraction at the end of the medical procedure.

The container comprises a complementary catch for the latch. Upon release from the cocked position, the foreportion is separated from the aft-portion to permit the needle to be retracted into the protective housing leaving the fore-portion to cover a major portion of the hole created when the cover is separated from the container.

The aft-portion of the needle/hub assembly comprises a hub which is affixed to a proximal end of a force storing memory element which is energized when the needle is pulled from the housing. Preferably, when the apparatus is used in blood sampling, the needle/hub assembly comprises a pathway for fluid flow to the memory element which also comprises a pathway for fluid flow.

The barrel/hub component comprises a hub which is affixed to the distal end of the memory element. In a preferred embodiment of the invention comprising a memory element which integrally incorporates a fluid flow pathway therethrough, the hub also contains a fluid flow pathway. For an application involving blood withdrawal to a receiving and blood withdrawing container (e.g. a vacuum blood draw tube, such as the Becton Dickenson Vacutainer), the pathway comprises a second needle tube which is similar to needles used in conjunction with Vacutainers. The barrel/hub also comprises a surface disposed about the memory element side of the hub which is joined to the open end of the outer cylinder of the housing/transport container to form the closed housing.

Though the memory element may comprise a plunger mechanism which draws a vacuum when the needle is extended to cock the apparatus for self-retraction or a spring, the memory element is preferably an elastic tube in blood sampling embodiments. It should be noted that use of an elastic tube provides opportunity for use of the tube to transport fluid as a tube connected at its ends and stretched therebetween maintains a patent pathway even when stretched. For the elastic tube to be used as the fluid pathway, the tube material must be effectively inert to blood products. Latex is an example of such material.

It is noted that, except for needles which are captured as parts of injection molded parts and an extruded tube, all parts are injection molded.

In a preferred embodiment, the inner cylinder is frangibly separable from the outer cylinder at the closed end. The hole made by separating the two cylinders is preferably substantially and permanently filled by a part of the foreportion of the needle/hub assembly as part of the cocking procedure.

Cocking of the release mechanism is triggered for release by depressing a compliable or compressible portion of the outer cylinder. That portion of the outer cylinder is protected from inadvertent depression by the protective flap. The flap is retained to protect the portion, for example by a snap-in groove connection, and removed by a simple flipping movement of a thumb or forefinger. The flap is preferably molded as an integral part of the outer cylinder connected thereto by a living hinge.

In a catheter insertion embodiment, the invention comprises a housing/transport receptacle, a needle/hub component and a housing closure module. In preferred embodiments, apparatus of the instant invention require as few as three injection molded parts, each part being representative of the receptacle, the element and the housing closure module mentioned above.

The housing/transport receptacle is preferably molded as a single multi-cylinder part. The part consists of two cylinders, an inner cylinder and an outer cylinder, and a protective flap connected by a living hinge to the outer cylinder. The inner and outer cylinders are mutually closed at one end and open at the other ends. The inner cylinder forms a needle cover which has an attachment (e.g. a female threaded or bayonet coupling) for joining to a male connection to provide a separable attachment to the needle/hub element. The outer cylinder of the housing/transport receptacle is preferably hermetically sealed to the housing closure module to form a closed housing, capable of being used as a transport package by maintaining needle sterility until opened at the beginning of a medical procedure.

The needle/hub element is preferably formed as a single injection molded part about a medical needle. The element comprises (a) the medical needle, (b) a fore-portion of the part more proximal to the sharp end of the needle and molded about a predetermined segment of the needle and (c) an-aft portion which is more distal from the sharp end of the needle and also molded about the needle.

The fore-portion is juxtaposed with a portion of the elongated length of the needle but slidably free of the needle after the molding process. The fore-portion comprises the male connection which is separably affixed to the needle cover during assembly. The fore-portion also comprises at least one latch which locks to a portion of the receptacle when the needle is pulled forth from the receptacle for use. During the pull, the fore-portion is securely affixed to the aft-portion. The aft-portion is firmly and securely affixed to the needle in the molding process. The act of pulling the fore-portion, therefore, results in a needle portion of the needle/hub element being emplaced in a position for use. Pulling the fore-portion fully to a locked position cocks the needle portion in position for release and retraction at the end of the medical procedure.

The receptacle comprises a complementary catch for the latch. Upon release from the cocked position, the foreportion separates from the aft-portion causing the needle to be retracted into the protective housing/transport receptacle.

Though the memory element may comprise an elastic tube or a spring, the currently preferred memory element comprises a piston part similar to pistons used in disposable syringes. As it is important to provide a blood flash viewing means in IV catheter insertion apparatus, a part which is intermediate between the needle and plunger apparatus comprises a translucent or transparent section into which blood is selectively permitted to flow and be seen by an operating technician.

Accordingly, it is a primary object to provide a novel and improved blood withdrawal device comprising a housing which maintains sterility of a medical needle and other internal parts of the device until use and which automatically fully retracts the needle into the housing after use.

It is a key object to provide the blood withdrawal device with an attached barrel for a blood acquisition vacuum tube (e.g. a Vacutainer made by Beckton Dickenson).

It is another key object to provide a needle cover for the device which is made as a part of the housing, but which is frangibly separable from the housing, thereby providing an exit pathway for the cover and the needle.

It is an important object to provide a means for releasing a cocked needle assembly by distorting a portion of the housing rather than requiring a button or other mechanical device to project through the housing wall.

It is also an important object to protect the portion which is distorted from being distorted during insertion and use of the needle and to remove the protection with a single digit motion immediately prior to retracting the needle.

It is an object to provide parts disposed at each end of the device which facilitate manually extending the needle for use.

It is another primary object that the device be usable but once and the needle be safely enclosed when retracted.

It is a very important object that the device be made with as few injection molded parts as possible.

It is therefore an important object that the device be made from as few as three injection molded parts (and as few as three extruded parts).

It is also an important object that a part used to pull the needle, latch the needle assembly into a cocked position, and separate to release the needle, for subsequent retraction, be moldable in a single molding step.

It is an object to provide an embodiment of the invention comprising a latch which is releasable by franging a section of the needle assembly.

It is a significant object to provide a manufacturing method for assembly of the device which is compatible with automatic assembly equipment.

It is an object to provide a force storing memory element which stores energy as the needle assembly is cocked and which provides retracting force upon release of the needle assembly.

It is a meaningful object to provide a memory element which comprises an enclosed fluid flow pathway for withdrawn blood.

It is a consequential object to provide an essentially closed pathway for regurgitant blood flow during retraction.

It is an object to provide a means for connecting the needle cover to the needle assembly during device manufacture which does not put undue stress upon a frangible part.

It is an object to provide a blood withdrawal device which is simple to use.

It is still another object to provide a means for seeing a blood "flashback" within the device as influent blood courses into the device from a pierced blood vessel.

It is yet another primary object to provide a novel and improved IV catheter insertion apparatus comprising a housing which maintains sterility of a medical needle, a catheter and other internal parts of the apparatus until use and which automatically fully retracts the needle into the housing after use.

It is a key object to provide the blood withdrawal apparatus which provides for containment of blood exiting the catheter immediately upon retraction of the needle.

It is another key object to provide a needle cover for the apparatus which is made as a part of the housing, but which is frangibly separable from the housing, thereby providing an exit pathway for the cover and the needle.

It is an important object to provide a means for releasing a cocked needle assembly by distorting a portion of the housing rather than requiring a button or other mechanical apparatus to project through a wall of the housing.

It is also an important object to protect the portion which is distorted from being distorted during insertion and use of the needle and to remove the protection with motion of a single digit immediately prior to retracting the needle.

It is an object to provide parts disposed at each end of the apparatus which facilitate manually extending the needle for use.

It is another primary object that the apparatus be usable but once and the needle be safely enclosed when retracted.

It is a very important object that the apparatus be made with as few molded parts as possible.

It is therefore an important object that the apparatus be made from as few as three injection molded parts (and as few as three extruded parts).

It is also an important object that a part pulled to extend the needle, latch the needle assembly into a cocked position, and separate to release the needle, for subsequent retraction, be molded in a single molding step.

It is an object to provide, in one embodiment of the invention, a latch which is releasable by franging a section of the needle assembly.

It is a significant object to provide a manufacturing method for assembly of the apparatus which is compatible with automatic assembly equipment.

It is an object to provide a force storing memory element which stores energy as the needle assembly is cocked and which provides retracting force upon release of the needle assembly.

It is a consequential object to provide an essentially closed pathway for regurgitant blood flow upon and during retraction.

It is an object to provide an IV catheter insertion apparatus which is simple to use.

It is still another object to provide a means for seeing a blood "flashback" within the device as influent blood courses into the device from a pierced blood vessel.

These and other objects and features of the present invention will be apparent from the detailed description taken with reference to accompanying drawings.

BRIEF DESCRIPTION OF THE DRAWINGS

FIG. 18 is a longitude section of a portion of the device showing the alternate needle/hub embodiment in three different positions in the device.

FIG. 19 is a section similar to the section seen in FIG. 18, but rotated 90°.

DETAILED DESCRIPTION OF THE ILLUSTRATED EMBODIMENTS

In this description, unless a specific object is referenced, the term proximal is used to indicate the segment of a device normally closest to the patient when it is being used. In like manner, the term distal refers to the other end. Reference is now made to the embodiments illustrated in FIGS. 1–23 wherein like numerals are used to designate like parts throughout. Generally parts having similar form and function to parts earlier cited are enumerated with primes numerals of the earlier cited parts.

Figure 1:
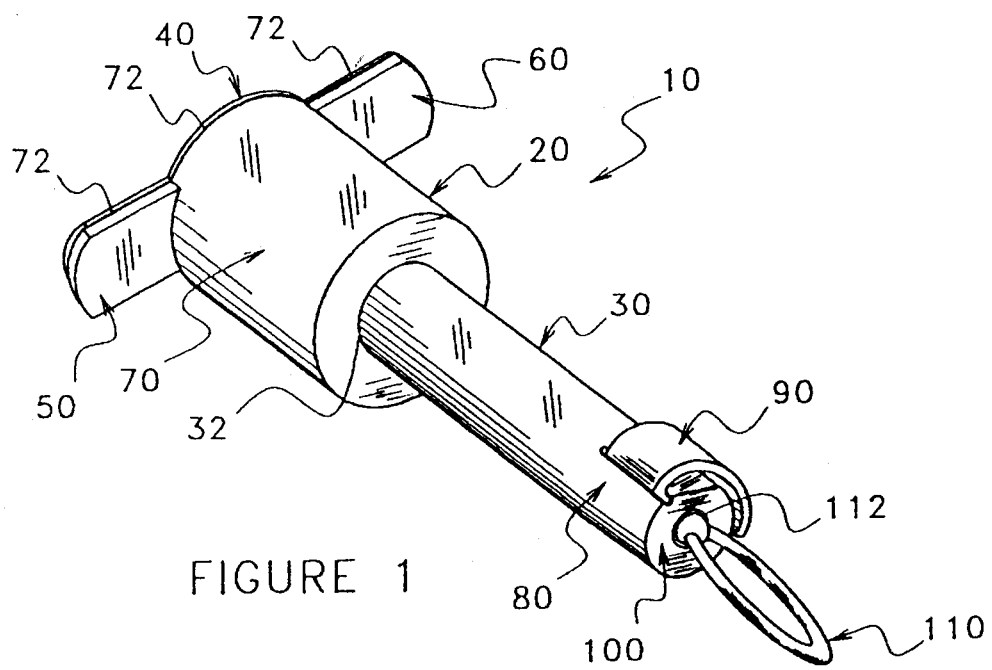
FIG. 1 is a perspective of a sealed blood withdrawal device, showing the outside of the device housing.

Reference is now made to FIG. 1 wherein an embodiment according to the invention of a blood withdrawal device 10 is seen. As seen in FIG. 1, device 10 comprises a barrel section 20 and a needle containment section 30. In a completely assembled device, section 20 is securely and hermetically sealed to section 30 along circular line 32.

Barrel section 20 comprises a planar seal 40 and a pair of left and right ear or handle parts, designated 50 and 60, respectively, and a hollow barrel 70. Planar seal 40 is adhesively attached to barrel section 20 within a plane area defined by continuous line 72 such that the hollow of barrel 70 is maintained in a sterile condition prior to use. To use device 10, seal 40 is manually removed. Of course, a different kind of seal may be used, such as a snap-on part which may be molded as a tether-attached part of section 20. The snap-on part is not shown, but production of such parts is well known in the art. A more detailed description of the internal parts of barrel 70 is provided hereafter.

Needle containment section 30 comprises an elongated tube 80, a flap 90, a proximally facing front face plate 100 and a pull-ring 110. Importantly, it should be noted that pull-ring 110 is separable from front face plate 100 at a frangibly detachable segment 112, which is described in more detail hereafter.

Figure 2:
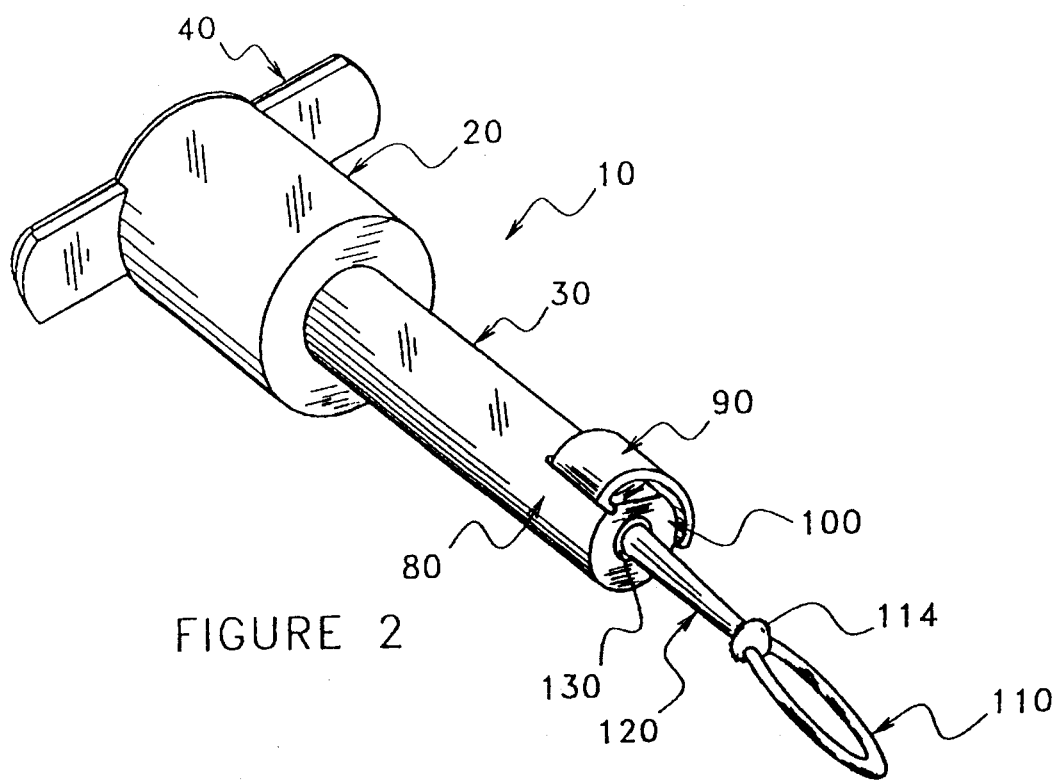
FIG. 2 is a perspective of the blood withdrawal device seen in FIG. 1 from which a needle cover and associated needle (not shown) have been pulled by first frangibly breaking away the needle cover from a portion of the housing.
Figure 3:
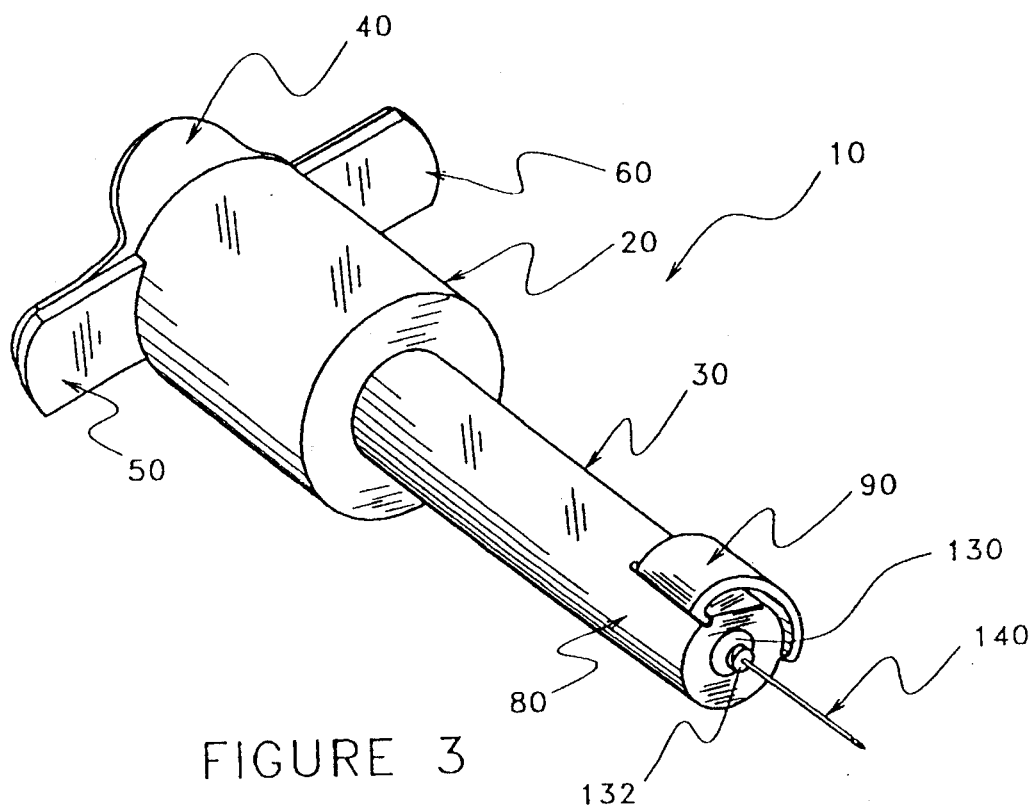
FIG. 3 is a perspective of the blood withdrawal device seen in FIG. 2 showing a needle bared by cover removal and a partially removed seal which covered and protected the internal portion of a blood withdrawal vacuum tube barrel, relative to the needle.
Figure 4:
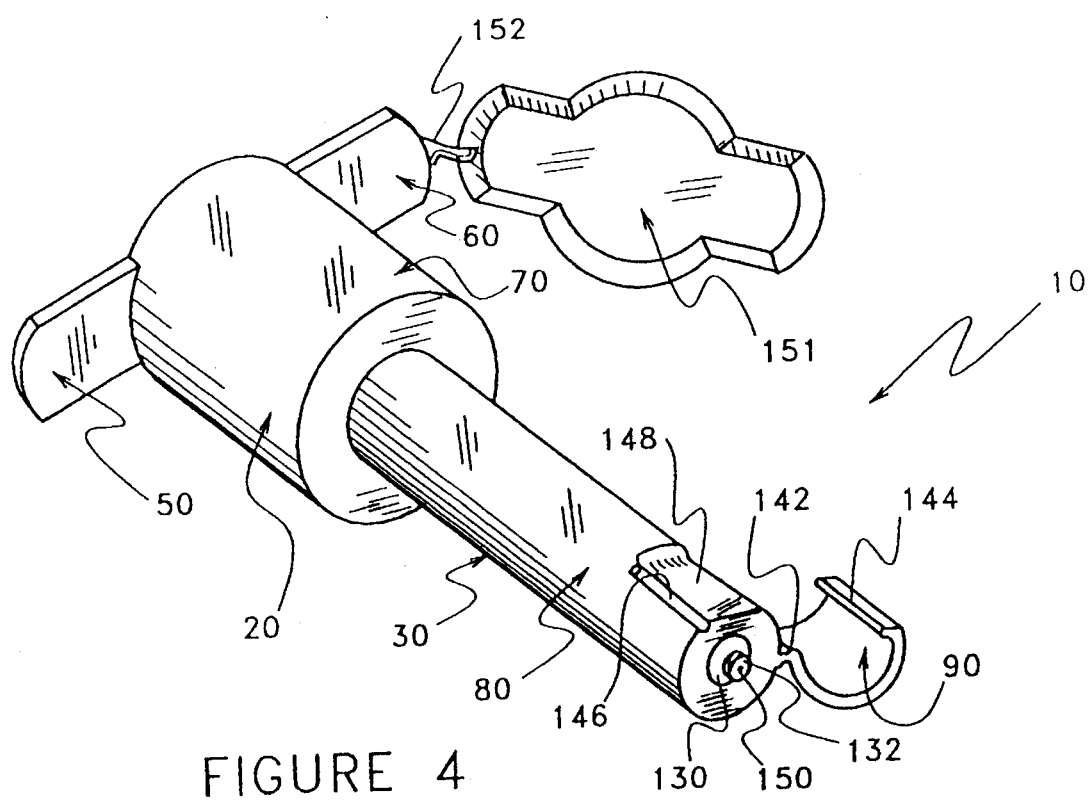
FIG. 4 is a perspective of the blood withdrawal device showing displacement of a flap, seen in place in FIG. 3, the displacement permitting an area of the housing previously under the flap to be distorted, the distortion resulting in retraction of the needle into the housing.
Figure 5:
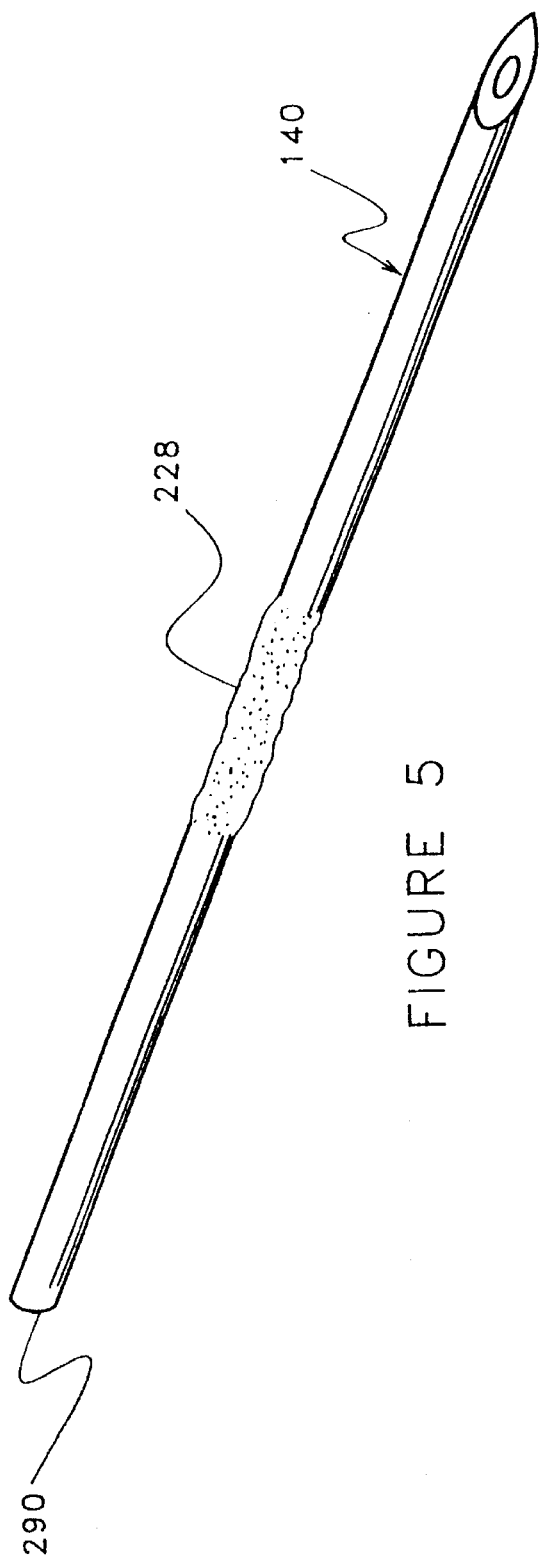
FIG. 5 is a greatly magnified perspective of a medical needle having a portion of the needle treated with a mold release.

Steps related to the use of device 10 are seen in FIGS. 2–4. In FIG. 2, pull-ring 110 has been detached from front face plate 100. Detachment of segment 112 produces a ragged collar 114. As pull-ring 110 is advanced from face plate 100, a needle cover 120 which is firmly affixed and integrally molded with pull-ring 110 appears through a hole created by removal of collar 114. Once pull-ring 110 is fully extended, a yoke 130 snaps into place about the hole produced by removal of collar 114. Structure of yoke 130 and related parts are disclosed in more detail later.

A next step is to remove seal 40 from barrel section 20. Seal 40 is seen to be in process of being removed in FIG. 3. In a next step, pull-ring 110 and needle cover 120 are removed from device 10. Needle cover 120 is preferably attached to a hub 132 by a rotatably detachable coupler, such as by a threaded or bayonet type connector. In any event, the coupling attachment between hub 132 and cover 120 must be able to support a pull force at least as great as a retarding force imposed in the opposite direction by a retracting mechanism which is energized by the pull extending cover 120 until engagement of yoke 130. As seen in FIG. 3, a hollow medical needle 140 is bared upon removal of cover 120.

As best seen in FIG. 4, flap 90 comprises a living hinge attachment 142 to elongated tube 80. Flap 90 also comprises a hook latch 144 which is normally engaged in a groove 146 proximally disposed in tube 80. Located flap 90, when disposed in groove 146 is a deformable area 148 of tube 80. While flap 90 is disposed and latched into groove 146, area 148 is fully protected from any deformation. Thus, during a medical blood withdrawal procedure, flap 90 is latched into groove 146. Once a blood acquisition procedure has been completed, flap 90 is rotated by action of a single digit after which needle 140 may be retracted by depressing area 148. Retraction places needle 140 safely inside tube 70. Only access to the inside of tube 70 and to needle 140 is a hole 150 in hub 132 which is the essentially the same diameter as the cross sectional diameter of needle 140. Further, as is explained later, needle 140 is securely held well away from hole 150. Retraction mechanisms for needle 140 are described in detail hereafter.

Also seen in FIG. 4 is a snap-on cover 151 affixed by a tether 152 to handle 60. Cover 151 is an alternative embodiment to seal 40. Cover 151 has the advantage of not requiring a cover part to be made separately from barrel section 20. However, to provide assurance that cover 151 has not been opened previous to a procedure to which device 10 is uniquely dedicated, an additional seal, such as a shrink wrap about exterior edges of cover 151 and related parts of handles 50 and 60 and tube 70 should be used. Making of parts attached by tether is well known in the art.

Figure 6:
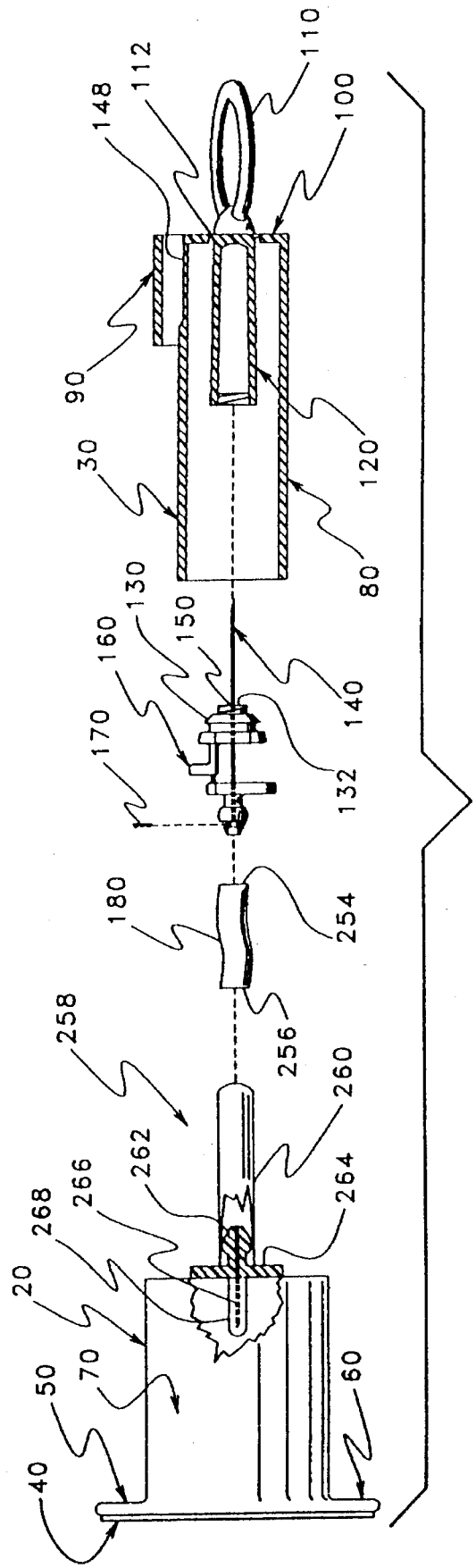
FIG. 6 is a an exploded side view of a blood withdrawal device with some portions segmented and other portions removed for better presentation.

Reference is now made to FIG. 6 wherein an exploded view of one embodiment of device 10 is seen to comprise needle containment section 30, a needle/hub part 160, a valve disk 170, an elastic tube 180 and barrel section 20. Attention is first drawn to needle/hub part 160 which is seen magnified for more clarity of details in FIGS. 7–9.

Part 160 comprises medical needle 140, a fore part 190 proximal to the sharp end of needle 140, a central part 192, and an aft part 194. Normally unseen extensions of needle 140 through part 160 is indicated by double dashed lines 196 and 198 for clarity of extent of needle 140 passage through part 160. Fore part 190 comprises yoke 130, hub 132, an annular groove 200, an annular stop 202 and an elbow shaped extension 204 which comprises an outwardly extending part 206. Central part 192 comprises a frangible bridge 208 and a support 210. Aft part 194 comprises a short shaft 212 and a tube hub 214. Part 160 is preferably molded as a single part with end-to-end continuity between parts 190, 192 and 194. Aft part 160 is firmly and securely affixed to needle 140 while fore part 190 is only slidably affixed and otherwise free to move along needle 140 when bridge 208 is franged.

Figure 7:
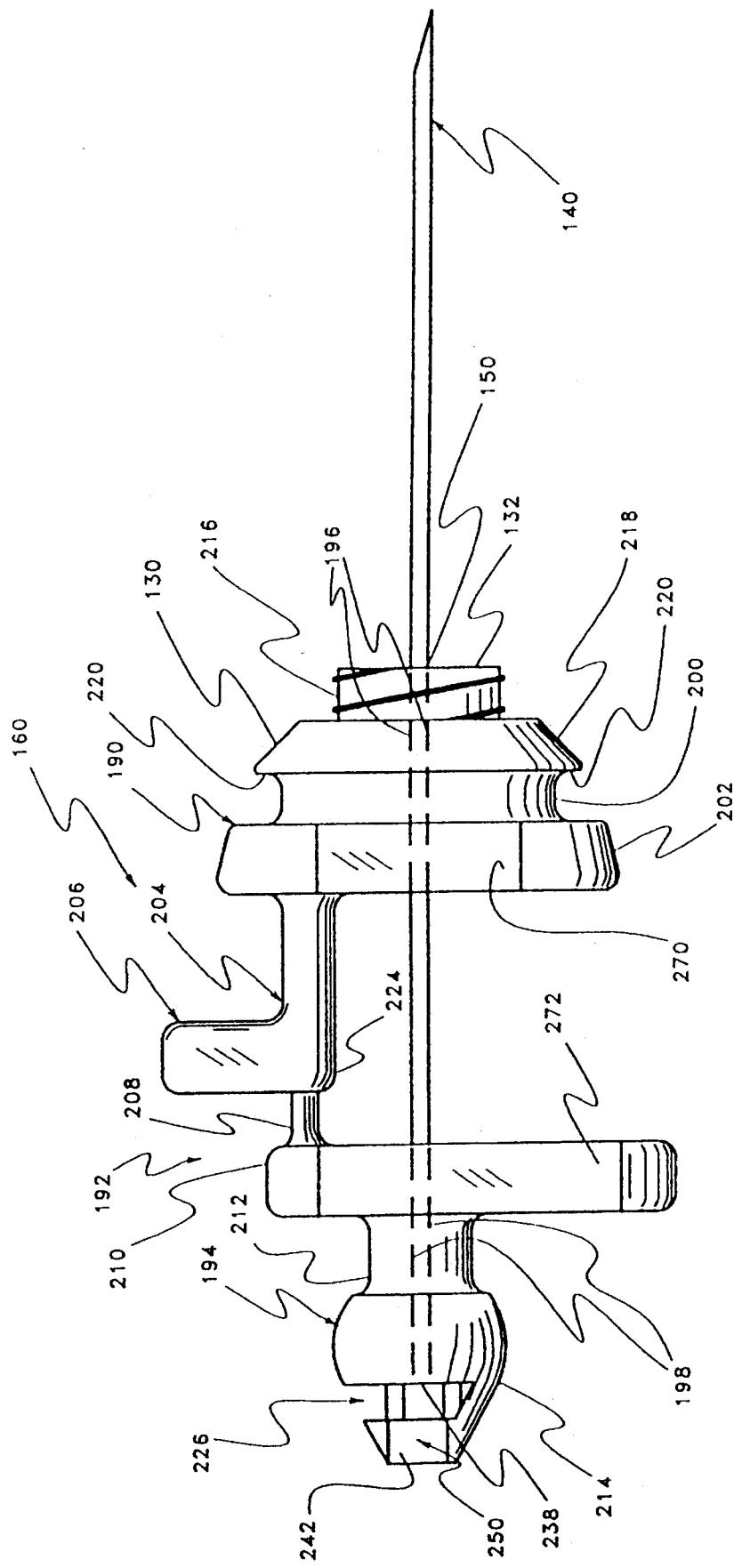
FIG. 7 is a lateral elevation of a needle/hub assembly which initially resides within the housing and is separably affixed to the cover.
Figure 8:
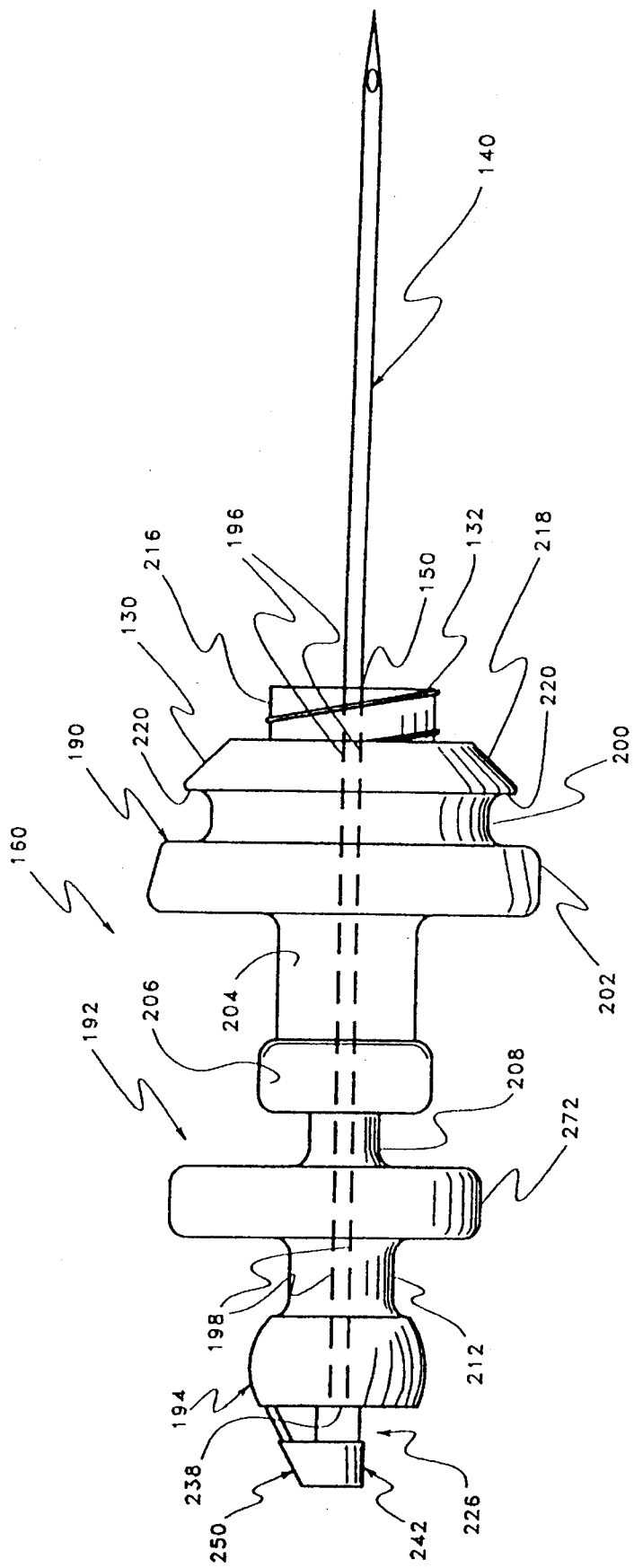
FIG. 8 is a top elevation of the needle/hub assembly seen in FIG. 7.
Figure 9:
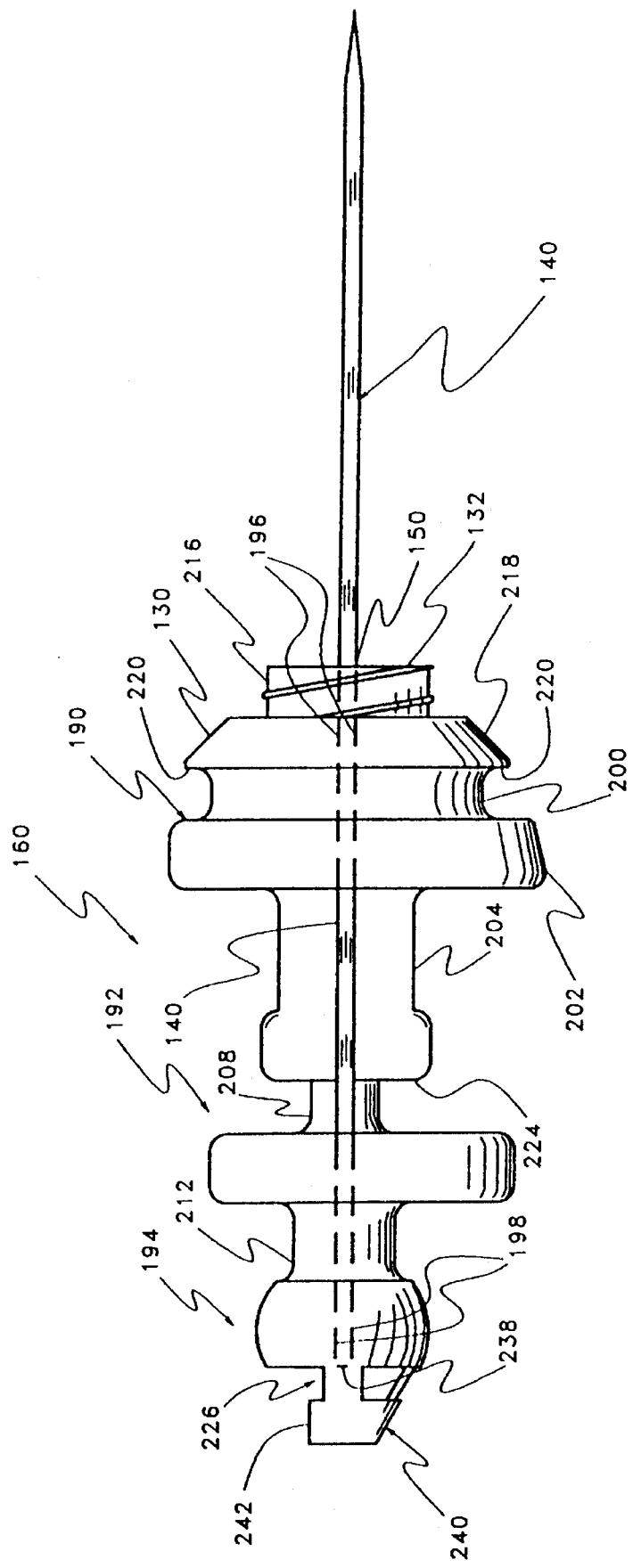
FIG. 9 is a bottom elevation of the needle/hub assembly seen in FIG. 7.

Hub 132 comprises a releasable connector component which may be in the form of a threaded surface 216 as seen in FIGS. 7–9. Yoke 130 comprises a sloped annular face 218 and a transverse latching surface ring 220 distal to and juxtaposed face 218. Groove 200 is interposed between and contiguous with ring 220 and stop 202. Function and use of yoke 130, groove 200 and stop 202 are described in detail hereafter.

As best seen in FIG. 7, extension 204 protrudes distally from stop 202 via a lateral bar 222 to an elbow 224 where extension makes an orthogonal bend to provide upward and outwardly extending part 206. Bridge 208 is a part which is narrow in both transverse dimensions to govern the degree of pressure required to frange bridge 208 from extending part 204. One of the surprising aspects of the instant invention is the force which may be placed upon bridge 208 when pulling against a force retaining memory element used in retracting needle 140 without breaking bridge 208 away from extension 204. Clearly, if even a nominal torque is place upon bridge 208 during a pull, bridge 208 might break. However, close tolerances maintained between needle 140 and fore part 190 reduce and keep such torque to a level which does not cause bridge 208 to break. The method for achieving close tolerances between needle 140 and fore part 190 is disclosed hereafter.

Bridge 208 is contiguous with support 210. Medially disposed about needle 140 and distally connected to support 210 is shaft 212. Tube hub 214, connected to shaft 212 provides a valve leaflet containment basket 226 wherein a one-way valve leaflet may be placed and trapped by a tube mounted on hub 214. Basket 226 is better seen in FIG. 10. Basket 226 comprises a slot formed by a distal facing side 228 and a proximal facing side 230, the two sides being connected by a bottom plate 232 and two side members 234 and 236.

Side 228 is a smooth planar face comprising a non-protruding blunt end 238 of needle 140. Also seen in FIG. 10 is a valve leaflet disk 240. Disk 240 is made of compliant synthetic resinous material which, under pressure, deforms to seal end 238 of needle 140 against regurgitant flow when pressure downstream from needle 140 is greater than upstream pressure. This seal is very important to contain blood within needle 140 upon retraction of needle 140. To assure a low resistance to flow from needle 140, disk 240 comprises a plurality of raised feet which space the distal side of valve disk 240 away from side 230. That spacing and various cuts, designated 242, 244, 246 and 248 in distal end 250 of aft part 194 provide a low resistance pathway for effluent flow from a patient.

Care should be taken that the diameter, designated by A arrows, of disk 240 is less than the sum of distances indicated by arrows B and C, but greater than B plus the diameter of needle end 238 to assure that regurgitant flow is always stopped, but disk 240 is not inadvertently held in an open condition by a tube stretched over hub 214.

Figure 10A:
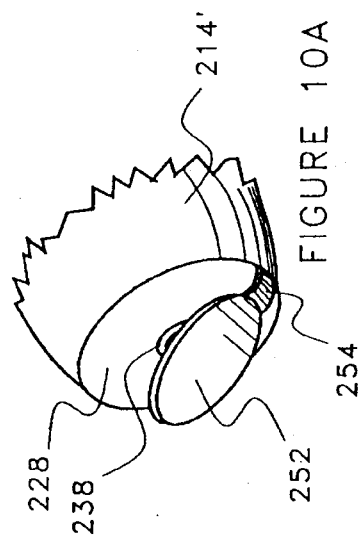
FIG. 10A is a perspective of a section of a needle/hub assembly showing a valve leaflet affixed by molding to the needle/hub assembly through a living hinge.
Figure 10:
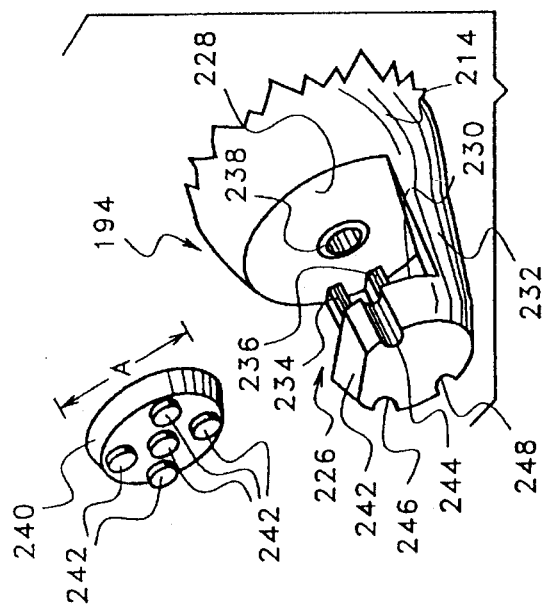
FIG. 10 is an exploded perspective of a section of the needle/hub assembly seen in FIGS. 7–9 and a valve leaflet which is used to restrict regurgitant flow form the device.

Another embodiment of a one-way valve is seen in FIG. 10A. If hub 214 is made of sufficiently resilient and compliant material, a leaflet valve may be integrally molded on the distal end of the hub. In the embodiment of FIG. 10A, a thin planar wafer 252 is integrally connected to a hub 214' (which is otherwise similar to hub 214) by a living hinge to curtail proximal flow through needle 140 at end 238 while being permissive to distal effluent flow.

In the embodiment seen in FIG. 6, retractive force is provided by a stretched tube. For this purpose, tube 180 is cut to a predetermined length allowing for displacement about a proximal and a distal hub and for a length of the tube which stretches when device 10 is cocked as needle 140 is pulled outward for use. Tube 180 comprises a proximal end 254 and a distal end 256. Tube 180 may be made from any elastic material which is effectively inert to blood and which can provide a return force of at least four pounds when stretched. It is preferred that the tube be capable of being stretched at least a length of four times its resting length. However, the currently preferred material is latex. Note that a needle of one inch in length should require a tube not greater in length than about one-half inch.

Barrel section 20 comprises a plurality of internally disposed parts, generally designated 258. Parts 258 comprise an elongated stabilizing key 260, a distal tube hub 262, an assembly plate 264, an rear delivery needle 266 and a needle cover 268.

Stabilizing key 260 is an elongated rod which stretches from assembly plate 264 to beyond stop 202 when device 10 is assembled and tube 180 is relaxed. Hub 262 is formed about needle 266 to provide a piercing entry to a low pressure collection tube (not shown) such as a Vacutainer®. As is standard practice in apparatus which is used to provide entry to low pressure collection tubes, a pierceable needle cover 268 is provided to deter leakage as collection tubes are replaced.

Figure 11:
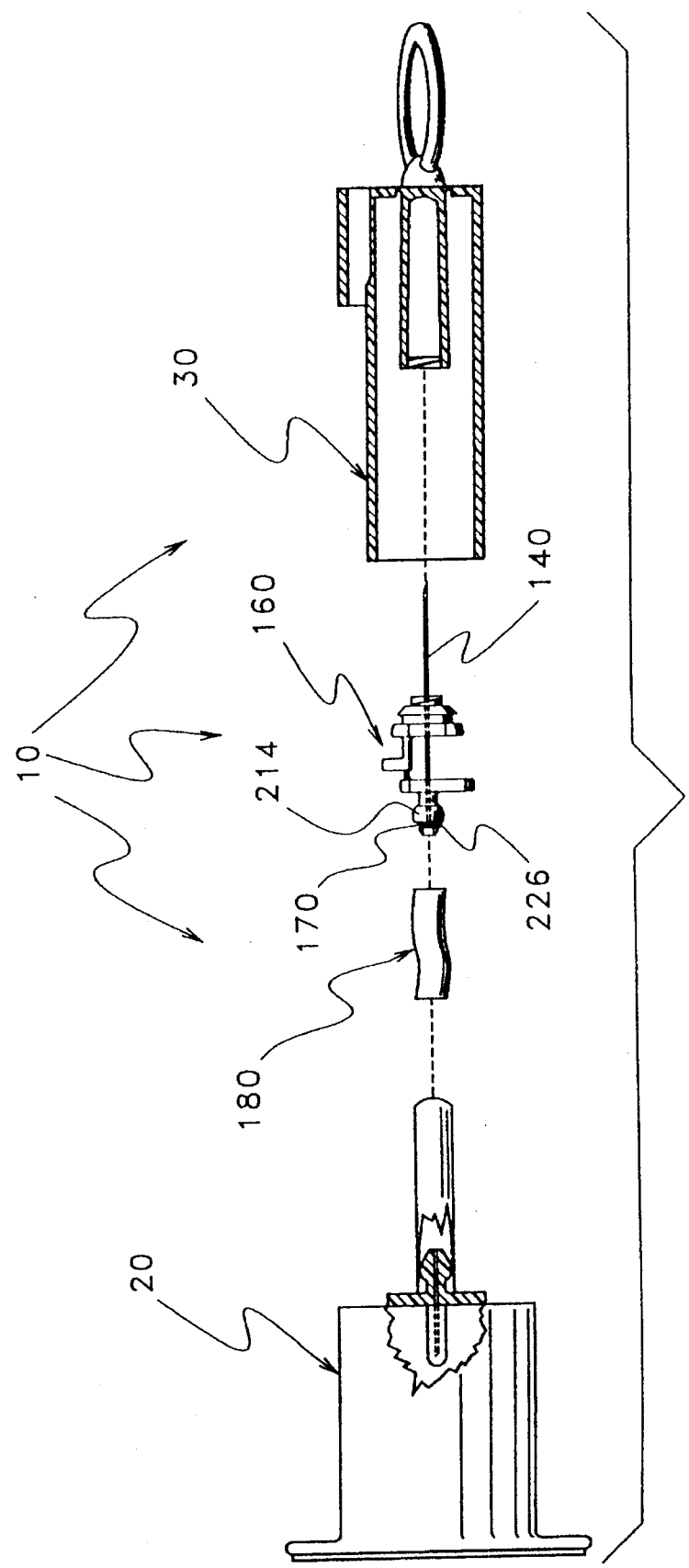
FIG. 11 is an exploded view of the device of FIG. 6 with a first assembly step completed.

FIGS. 6, 11, 12, 13 and 14 demonstrate simplicity of assembly of device 10. FIG. 6 is representative of parts in a preassembled configuration. Step one in assembly comprises insertion of valve disk 170 into valve containment basket 226 as seen in FIG. 11. Note that step one is not required when a valve leaflet such as a valve formed by wafer 252 is an integral part of tube hub 214'.

Figure 12:
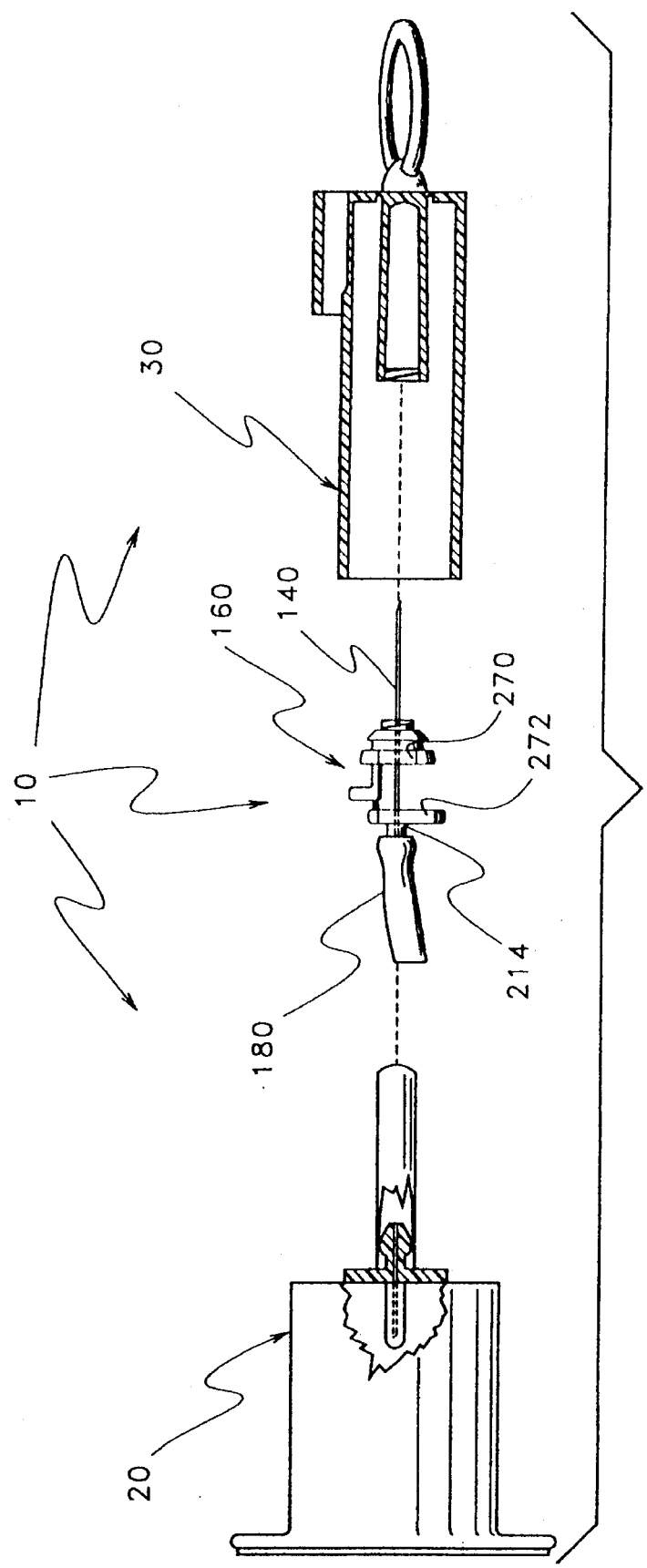
FIG. 12 is an exploded view of the device of FIG. 7 with a second assembly step, comprising attaching an elastic tube, completed.

Attachment of tube 180 to hub 214 (or hub 214' in the case of the embodiment seen in FIG. 10A) is seen in FIG. 12. To assure that tube 180 is securely affixed to hub 214 (or 214') it is recommended that an adhesive be applied to a proximal portion of hub 214 (or 214') immediately before tube 180 attachment. A suitable adhesive material should be used and care should be taken to assure that no inappropriate blood reactive material is allowed to contact areas where blood may flow. One adhesive which has provided satisfactory adhesion in models of the invention which have been reduced to practice is Duro Super Glue, manufactured and distributed by Loctite Corporation, Cleveland, Ohio 44128, commonly known as Super Glue, although other adhesive materials known in the art may also be used within the scope of the invention.

Figure 14A:
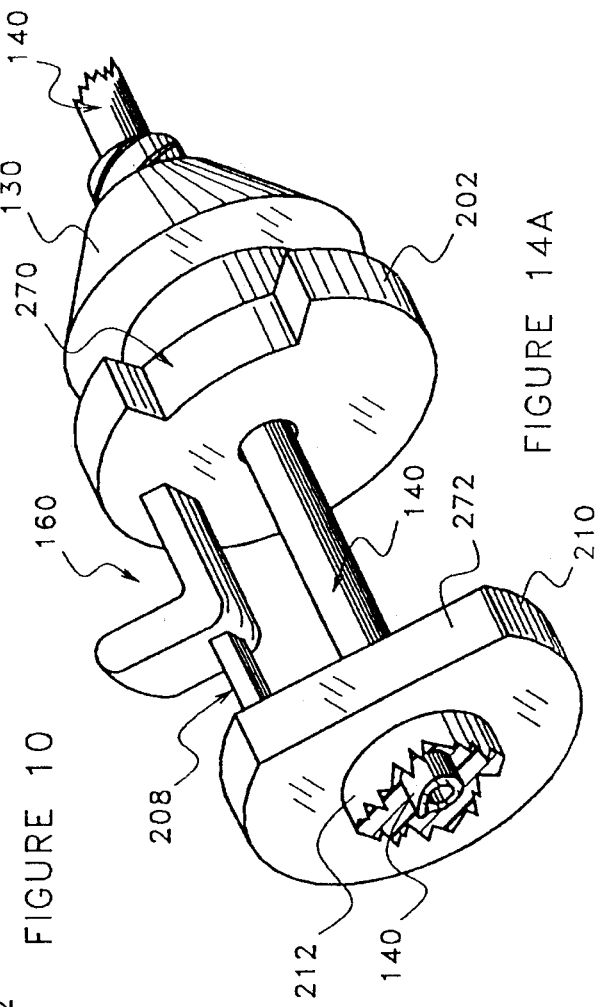
FIG. 14A is a perspective of a needle/hub assembly with portions removed for clarity of presentation.
Figure 13:
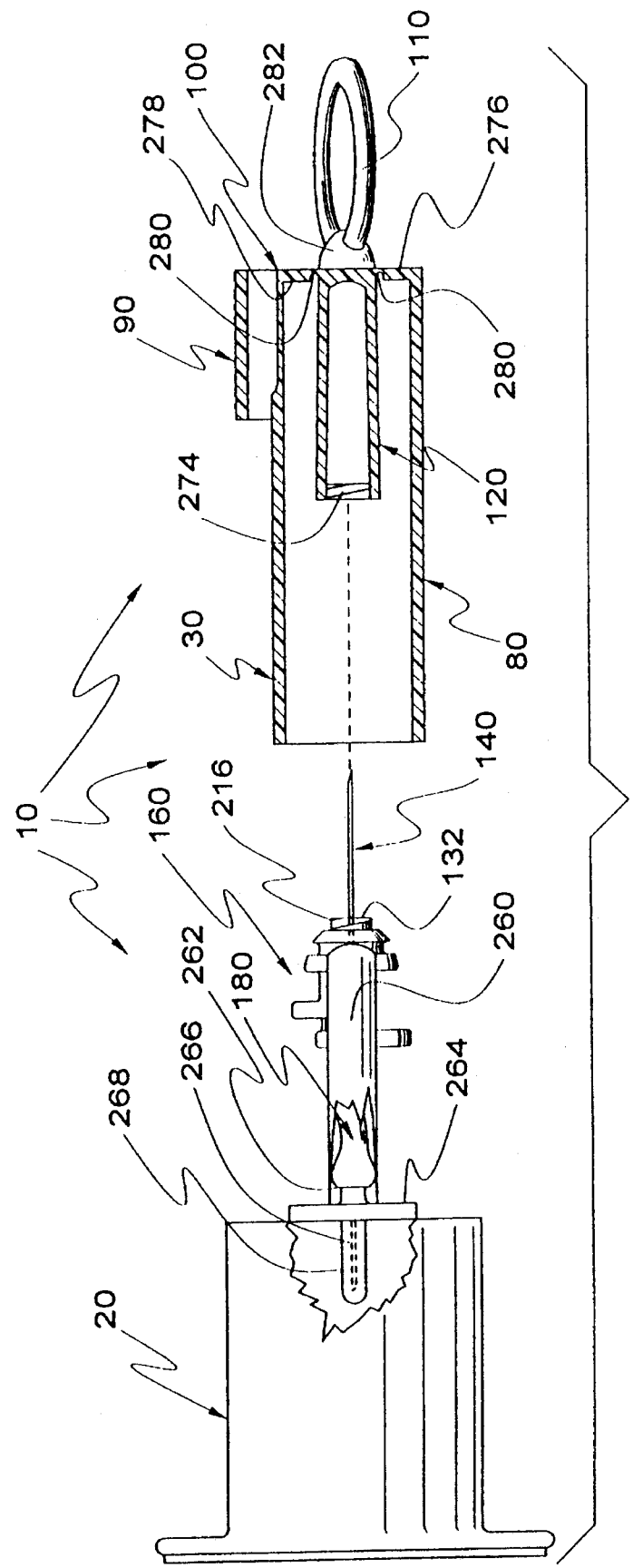
FIG. 13 is an exploded view of the device of FIG. 7 with a third assembly step of attaching the elastic tube to the barrel part. (Note that a perspective of a completely assembled device is seen in FIG. 1.)

Completion of a fluid flow path from needle 140 is seen in FIG. 13. Tube 180 is connected on distal end 256 to hub 262. At the same time stabilizing key 260 is engaged in a locking slot 270 (See FIG. 14A) disposed in annular stop 202. Key 260 is formed to slide laterally into and out of slot 270 and fit snugly therein when tube 180 is relaxed (i.e. during assembly). In this manner, no undue torque or rotational stress is placed upon frangible bridge 208 during assembly. To provide a pathway for key 260 past support 210, a material relieving flat 272 is formed along the plane of travel of key 260 in support 210.

As a next step needle containment section 30 is disposed about the assembled parts. Needle cover 120 comprises a female connecting segment 274 which is complementary to the male connector provided by hub 216. Cover 120 is preferably affixed by rotating section 30 relative to hub 216 although press-on connections which can withstand pull forces exerted by an elongating tube or spring or the like may also be used.

As needle cover 120 is connected to hub 216, tube 80 of section 30 engages assembly plate 264. Tube 80 is securely affixed to assembly plate 264 by adhesive or ultrasonic welding processes which are well known in the art of plastics assembly. In this manner, a hermetically seal is provided to protect needle 140. As such, sections 20 and 30, in combination provide a housing for needle 140 which may be used without additional packaging for transport.

Attention is now drawn to front face plate 100 of section 30. Face plate 100 comprises a proximal surface 276 and a distal substantially surface 278. Disposed in surface 278 is an annular groove 280. Groove 280 completely encircles the area where cover 120 integrally connects to plate 100 and a ring hub 282 which is integral with the proximal end of cover 120. Hub 282 also integrally connects ring 110 to section 130. Groove 280 is of sufficient depth in plate 100 to permit facile frangible separation by a positive tug, twist or pull on ring 110 while retaining sufficient material to provide a hermetically sealed container and a sturdy and safe transport container. Products having such seals are available in commerce.

Figure 15:
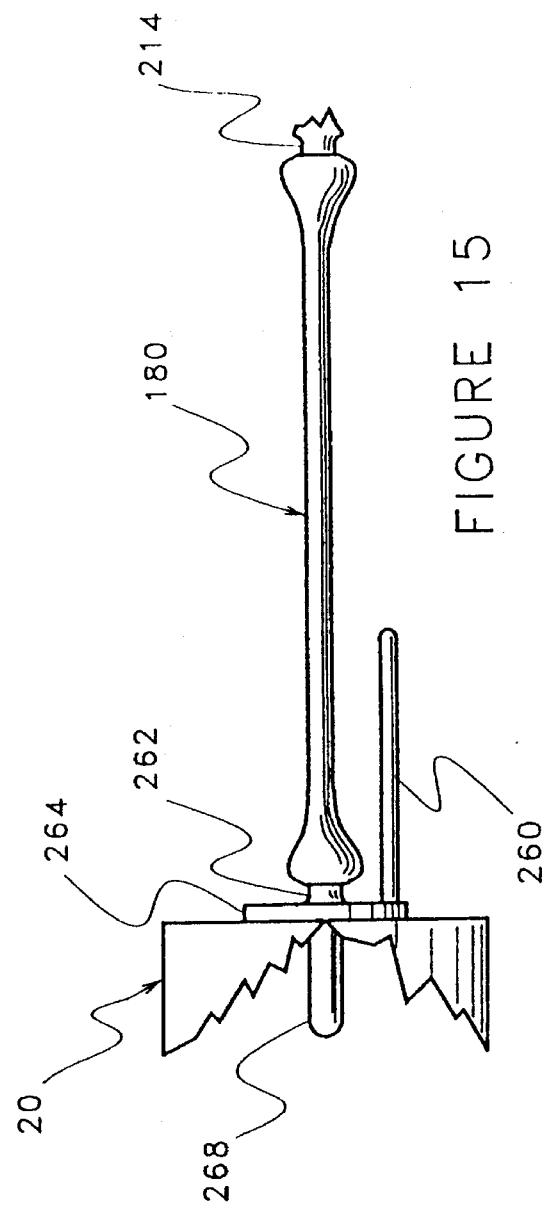
FIG. 15 is a lateral elevation of an elastic tube stretched between hubs of the barrel and needle/hub assembly parts.

Frangibly separating ring 110 and cover 120 from section 30, as seen in FIG. 2, causes tube 180 to be stretch between separating hubs 214 and 262 as is best seen in FIG. 15. Note that needle hub part 160 and, in particular, locking slot 270 is pulled away from key 260 by the same action. For this reason, it is advisable to make groove 280 and cover 120 somewhat asymmetric to minimize rotation during tube extension. One of the material attributes which permits tube 180 to be used to store energy to retract needle 140 and to act as a pathway for fluid communication between needle 140 and needle 266 is that the internal lumen of a tube remains patent when stretched. The diameter of the lumen is reduced but not closed as the tube elongates.

Figure 14:
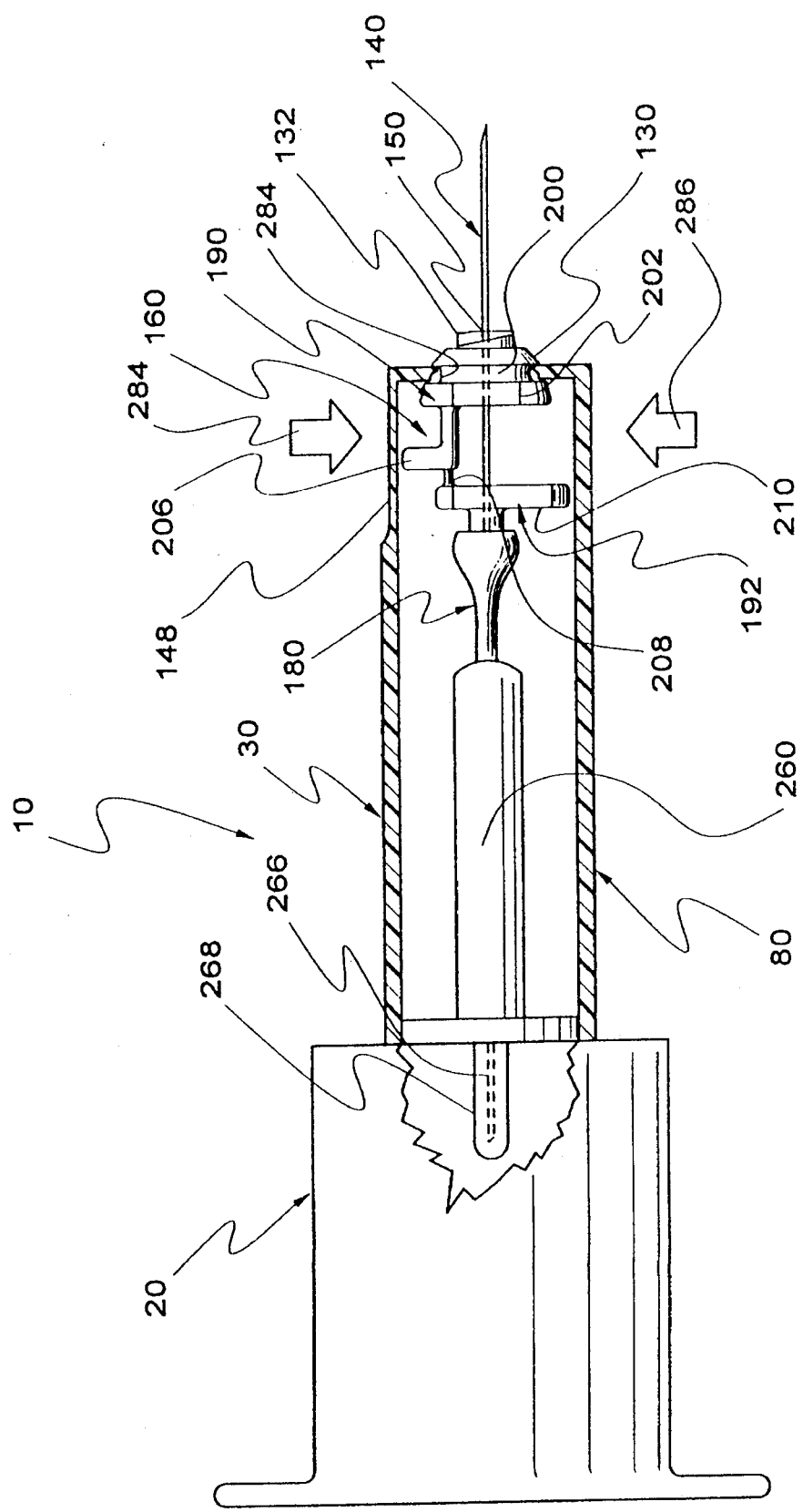
FIG. 14 is a section of a used device prior to retracting the needle.

When ring 110 and cover 120 are separated from section 30 by franging plate 100 at groove 280, an annular hole 284 is created in plate 100. As seen in FIG. 14, when needle/hub part 160 is pulled proximally, cover 120 and then yoke 130 are pulled through hole 284. The slanting annular surface 218 of yoke 130 as best seen in FIGS. 7–9, comprises a proximal diameter which is smaller than the diameter of hole 284 and a distal diameter which is larger than hole 284. However, the distal diameter is such that yoke 130 passes through hole 284 due to the "give" of material from which section 30 is made. Groove 200 has a width which permits plate 100 to be engaged therein when yoke 130 is pulled through hole 284. The proximal face of stop 202 has a diameter which is greater than hole 284 causing part 160 to be firmly affixed to plate 100 when yoke 130 passes through hole 284 as seen in FIG. 14.

Once the procedure involving needle 140 is completed, and preferably while needle 140 is yet disposed in a patient's blood vessel, needle 140 is automatically retracted. The retraction process involves (1) hingeably relocating protective flap 90 (as seen in FIG. 4) and (2) applying pressure upon part 206 through area 148 of tube 80 to frangibly separate fore part 190 from aft part 192 of by breaking bridge 208 of part needle/hub part 160.

Flap 90 is commonly released from attachment to tube 80 at groove 146 by inserting a thumb or finger under a portion of flap 90 and lifting. Bridge 208 is broken by applying pressure, preferably between a thumb and forefinger, in the direction of arrows 284 and 286. Franging forces (i.e. shear forces) are thus applied through area 148 to part 206 and an inferior portion of tube 80 to support 210. Note that substantially all other forces applied to bridge 208 are those of tension caused by longitudinal stretching of tube 180. For this reason, bridge 208 comprises a geometric shape which is conducive to breaking when imposed upon by shear forces, but capable of withstanding large amounts of tension.

One of the major reasons that substantially all of the forces placed upon bridge 208 during extending a retractive mechanism is a close tolerance held between needle 140 and fore part 190. As mentioned herebefore, part 190 is made to be free of needle 140 such that it can slide thereon. To maintain the tight tolerance and to provide an inexpensive method for manufacture of part 160, needle/hub part 160 is preferably molded as a unit about needle 140. Part 160 is preferably injection molded.

To permit fore part 190 to be molded about needle 140, yet remain slidably free, a thin coat of mold release is applied about needle 140 prior to molding. By applying a coat 288 of mold release in an area where fore part 190 is molded, fore part 190 remains only slidably attached to needle 140. Of course, at the distal end 290 of needle, aft part 194 is firmly and securely affixed by the molding process causing needle 140 to be retracted when tube 140, attached to aft part 194, is permitted to contract. Note that, when needle 140 is retracted through yoke 130 and hub 132, the only access into tube 80 is through hole 150 which has substantially the same diameter as needle 140. Of course, once needle 140 is retracted, it is irretrievably held inside tube 80 by a relaxed tube 180.

Except for needle 140, which is made of medical grade steel, needle/hub part 160 is made from a moldable material having sufficient tensile strength to withstand pull pressures of device 10 yet be facilely separated at bridge 208. As such, part 160 is preferably made synthetic resinous material, such as polyurethane, polypropylene or polyethylene. For an experimental device, the synthetic resinous material used was polyurethane sold as Quik Cast distributed by TAP Plastics, Dublin, Calif. 94568, however many currently commercially available materials may be used within the scope of the invention.

Barrel section 20 is likewise preferably made from synthetic resinous material. Barrel section is also preferably molded about rear delivery needle 266. The same material which is used in currently commercially available barrels used with vacuum based blood drawing tubes (e.g. Vacutainers) may be used. Needle cover 268 may be the same as Vacutainer barrel needle covers now in use.

Needle containment section 30 is preferably made by a single molded process. Mold material should be selected such that it provides sufficient material strength to engage and hold the hub 132 connection through the pull process, sufficiently flexible when made as a thin membrane to permit distort sufficient to break bridge 208, and frangibility for facile opening as at groove 280. The material is preferably a synthetic resinous material and may be polyethylene, although other materials meeting flexibility, medical compatibility and strength requirements may be used.

Figure 16:
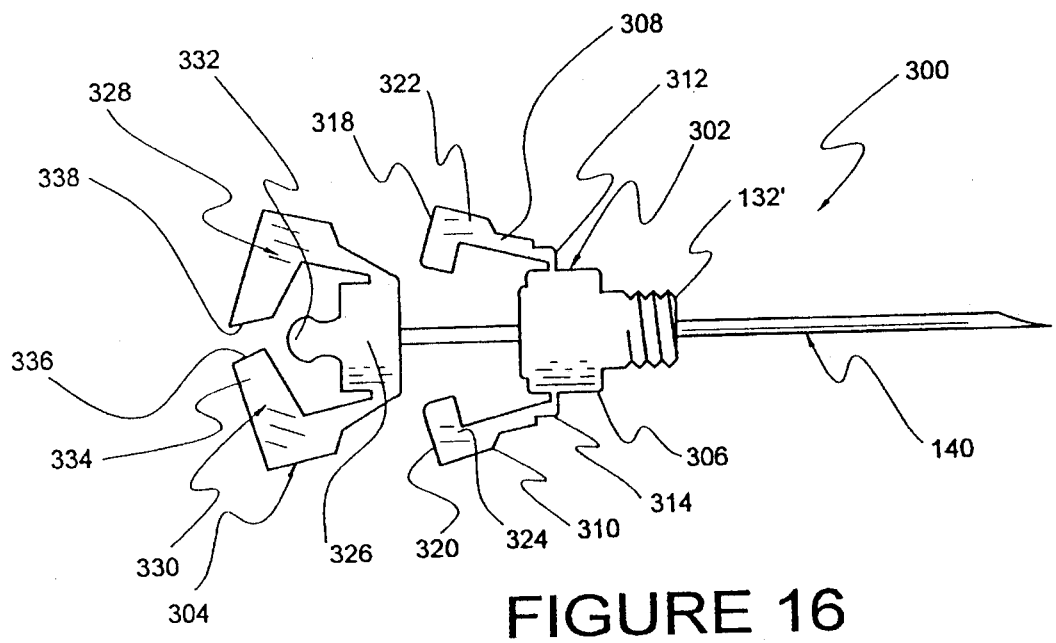
FIG. 16 is a side elevation of an alternative embodiment of a needle/hub assembly showing a first part which is molded about and securely affixed to the needle and a second part which is molded about the needle but which is free to slide longitudinally along the needle.

Reference is now made to FIGS. 16–20 which relate to another embodiment of the invention. This embodiment is similar to the embodiment seen in FIGS. 6–14 in general form and function, but does not depend upon a frangible part to release and retract the needle. As seen in FIG. 16, a needle/hub assembly 300 comprises two parts, designated forepart 302 and aft-part 304, which are formed about a needle 140. Parts 302 and 304 may be molded about needle 140 simultaneously. Part 302 is preferably molded about a segment of needle 140 to which a mold release has been applied, as earlier described. (See FIG. 5.)

Fore-part 302 comprises a central body 306 and a pair of outwardly extending wings or arms, individually designated 308 and 310. Each arm 308, 310 is connected to central body 306 by a biased hinge 312 and 314, respectively. The biasing of hinges 312 and 314 is preferably formed as a part of the molding process. Such hinges are well known in the art; as an example note hinges on telephone connectors. Each arm 308, 310 is biased to extend outwardly from central body 306 a predetermined distance. Disposed at the outer end 318, 320 of each arm 308, 310, respectively, is an inwardly projecting latching extremity 322, 324.

Central body 306 comprises a cover connecting hub 132' which is similar in form and function to hub 132. A portion 316 is disposed distal to hub 132' where hinges 312 and 314 are attached.

Aft-part 304 comprises a central body part 326, a pair of outwardly extending and biased wings or arms 328 and 330 and a tube hub 332. Wing 330 comprises an inwardly projecting strut 334 which ends at a clamping face 336. In opposing fashion, wing 328 comprises an inwardly projecting jaw 338. Function and use of the various parts of fore-part 302 and aft-part 304 are disclosed in detail hereafter.

Figure 17:
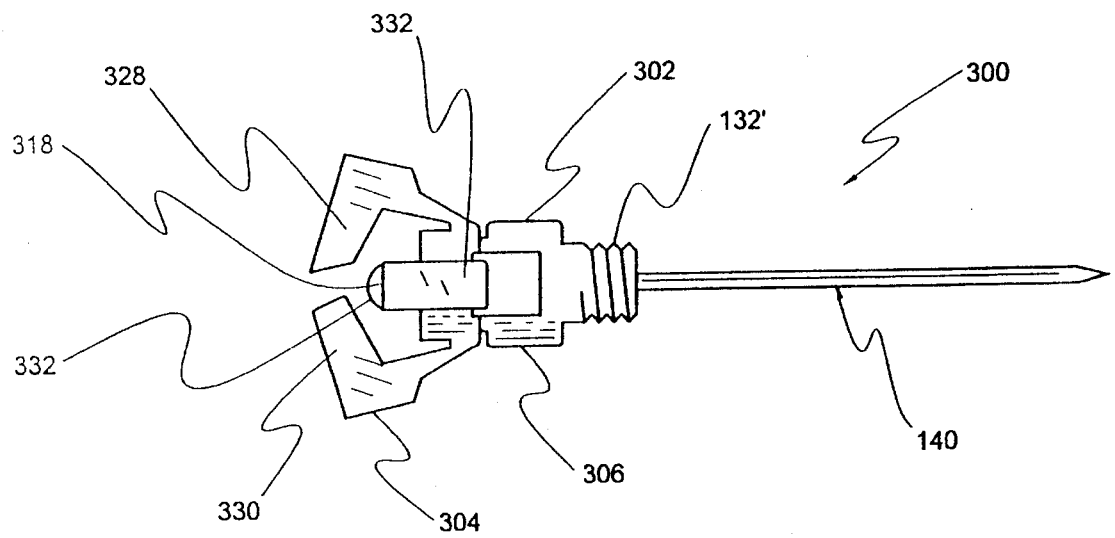
FIG. 17 is a side elevation of the embodiment seen in FIG. 16 with the slidable part moved to an adjoining position relative to the first part.

As mentioned earlier, fore-part 302 is preferably molded about needle 140, but not attached thereto, except by the natural engagement provided by materially surrounding the circumference of a portion of the needle. This permits forepart 302 to be rotated 90° and moved into linkable proximity with aft-part 304 as seen in FIG. 17.

Figure 21:
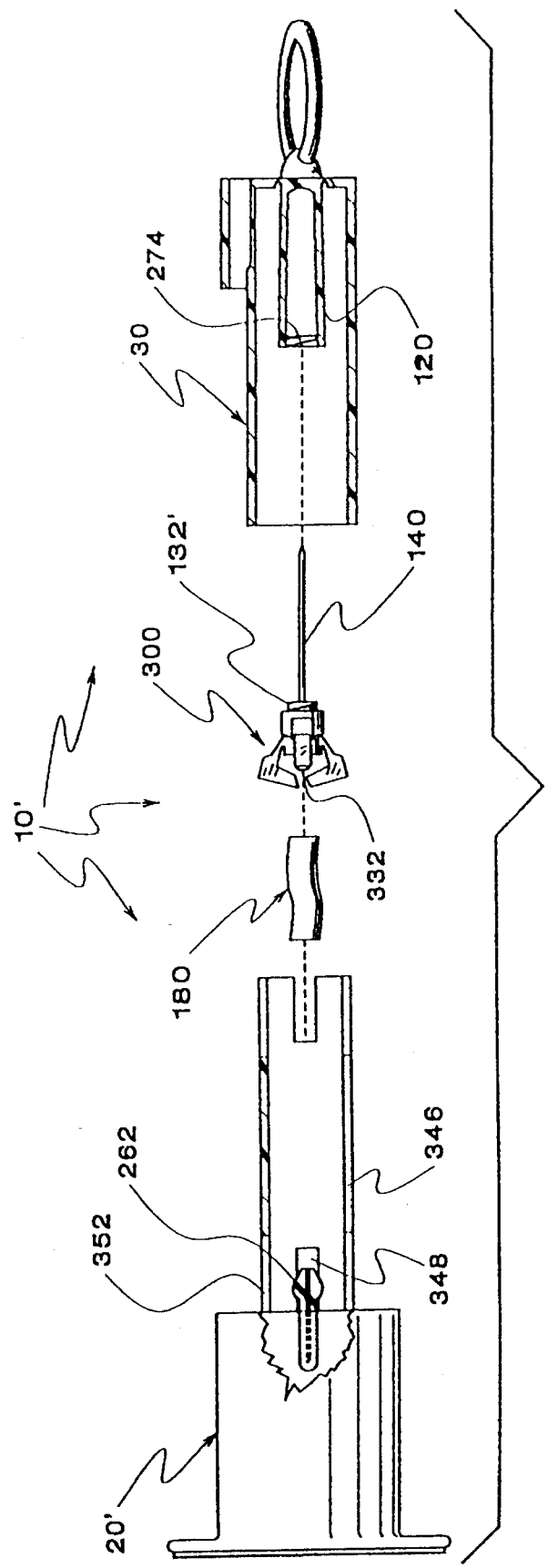
FIG. 21 is an exploded perspective of the device comprising the alternate needle/hub embodiment.

Parts content in this second embodiment of blood withdrawal device 10 is best seen in FIG. 21. This second embodiment comprises a barrel section 20', tube 180, needle hub assembly 300 and needle containment section 30.

Barrel section 20' is substantially the same as barrel section 20 except for the substitution of a guide-catch cylinder 340 integrally and medially disposed on a fore portion of barrel section 20' rather than stabilizing key similarly disposed upon barrel section 20.

Figure 20:
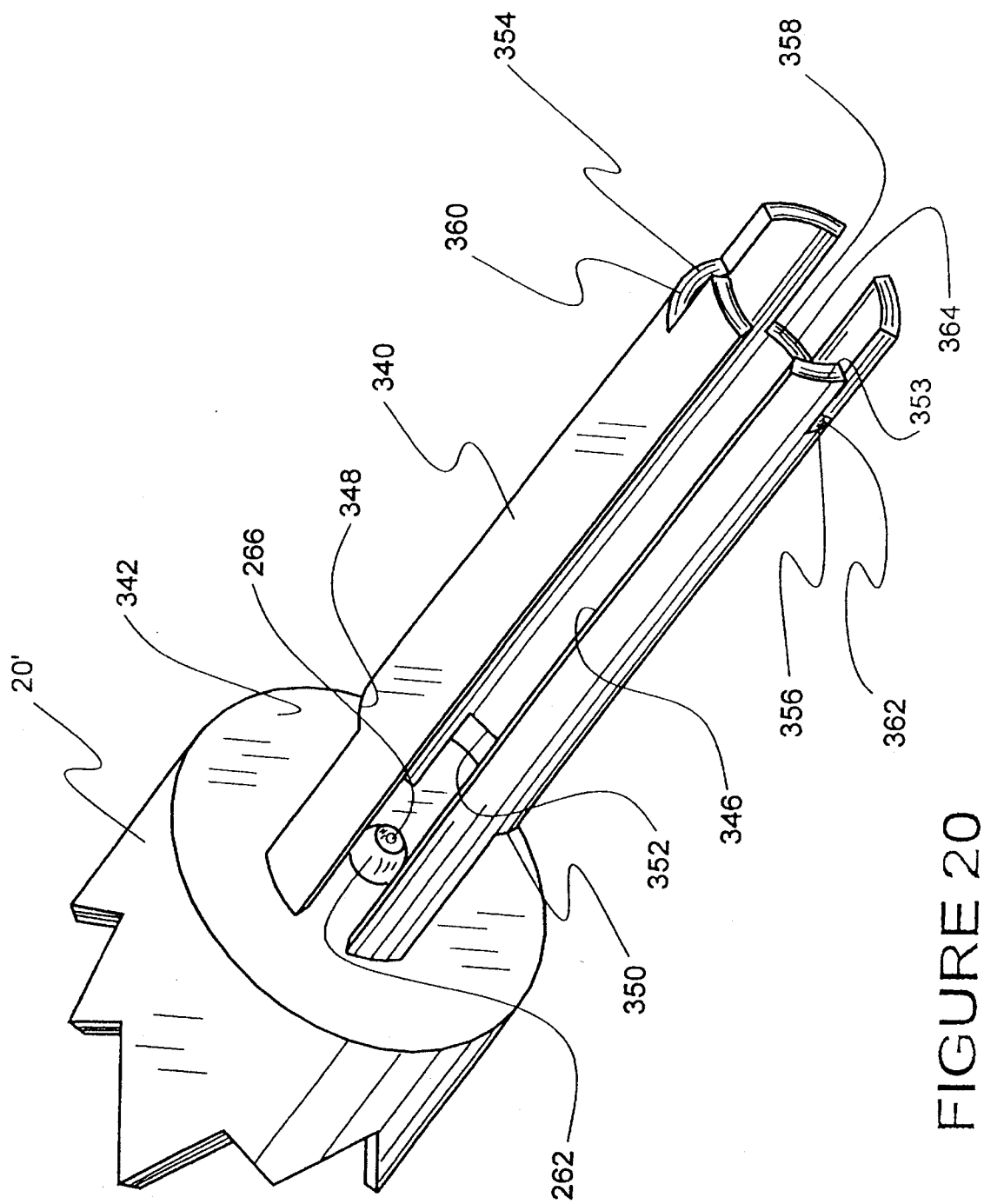
FIG. 20 is a perspective with some parts removed for clarity of a barrel section associated with the embodiment seen in FIGS. 16–20.

Guide-catch cylinder 340 is best seen in FIG. 20. As seen therein, barrel 20' comprises barrel 70, a substantially closed fore face 342 of barrel 70, distal needle hub 262, providing access to needle 266, and guide-catch cylinder 340. Guide-catch cylinder 340 is medially disposed upon face 342 and extends in elongated fashion in line with of needle 140 (not seen in FIG. 20). Hub 262 is medially disposed inside cylinder 340 along the same line.

Cylinder 340 comprises a plurality of slots which provide relief for outwardly biased members of parts 302 and 304, travel guide for assembly 300 and catch stops which selectively maintain parts of assembly 300 in a proximal position while needle 140 is in use. A first slot 346, disposed to act as a guide, extends the length of cylinder 340. In this embodiment device 10 is assembled to dispose a portion of wing 330 in slot 346.

Disposed at its distal end, cylinder 340 comprises a second slot 348 offset at 90° from slot 346 and having a length which is adequate for relief from compression of wing 308 when assembly 300 is distally disposed before use. Likewise, cylinder 340 comprises a third slot 350 similar to slot 348 and juxtaposed 180°, therefrom, to provide relief from compression of wing 310. A fourth slot 352 of cylinder 340 is distally disposed 180° from slot 346 and provides before-use relief from compression for wing 328. Should an outwardly biasing material be used in manufacture of assembly 300 which does not take a set after time between assembly and use, it is not necessary to provide slots 348, 350 and 352.

Cylinder 340 provides openings for four slots at its proximal end 353, i.e. slots 346, 354, 356 and 358. As mentioned earlier slot 346 provides a guide for assembly 300 by containment of wing 330. Longitudinally slots 354 and 356 are respectively aligned with slots 348 and 350. Slot 354 comprises a catching edge 360 for end 318 of wing 308 while slot 356 comprises a catching edge 362 for end 320 of wing 310. Slot 358 is aligned with slot 352 and provides a catching edge 364 for wing 328 as is described in detail hereafter. Each slot has a depth such that in combination latch portions of wings 308, 310 and 328 occur substantially simultaneously.

Latching operation of elements of assembly 300 is best seen in FIGS. 18 and 19. Each of FIGS. 18 and 19 are divided by dashed lines into three sections (A, B and C) to demonstrate operation of fore-part 302 and aft-part 304 of assembly 300 at different positions along the length of cylinder 340. Note that wings 328 and 330 are vertically disposed in FIG. 18. Wings 308 and 310 are vertically oriented in FIG. 19 as parts of assembly 300 in FIG. 19 are rotated by 90° relative to parts in FIG. 18.

It is particularly important to note that wing 328, as seen in FIGS. 18A and 18C, extends superiorly from central body part 326 along a line 366 to pivot arcuately upward at arc 368 to join a superior line 370. Further, line 370 ends at a latch point 372. From latch point 372, the shape of wing 328 is further defined by an inwardly progressing line 374 and an acutely connected line 376 which, combination, demarcate jaw 338.

A seen in FIG. 18A, wherein assembly 300 is residing distally within cylinder 340 and tube 80, wing 330 is free to move in the longitudinal direction of needle 140 guided by slot 346. In the same assembly 300 position, wing 328 is disposed in an uncompressed or relaxed state within slot 352. When assembly 300 is pulled proximally to a cocked and useful state as seen in FIG. 18C, assembly 300 passes through an intermediate state seen in FIG. 18B. As assembly 300 is moved proximally from the state seen in FIG. 18A, the form of wing 328 formed along line arcuate line 368 permits wing 328 to be collapsed such that line 370 of wing 328 coincides with the cylindrical inner surface of cylinder 340. In this manner, the aft-part 304 of assembly 300 is facilely allowed to move through cylinder 340.

Note that compression of wing 328 as seen in FIG. 18B causes jaw 338 to compressively pinch tube 140 stopping any flow of liquid therethrough while wing 328 is between slots 352 and 358. Moving assembly 300 proximally to the position seen in FIG. 18C permits wing 328 to be once more relieved as it is biased to enter slot 358. Once there, a latch formed at latch point 372 and along line 374 is caught by edge 364, firmly retaining assembly 300 with tube 140 in a stretched condition.

Referring now to FIG. 19, device 10 has been rotated 90° clockwise relative to a view of the needle 140 end of the device. In FIG. 19 wings 308 and 310 are vertically oriented. Each arm 308, 310 resides in a non-compressed state in slots 348 and 350, respectively. Arm 308 comprises an arcuate surface 378, similar to the wing 328 arcuate surface along line 368, which provides a facile release from slot 348. Arm 310 comprises a similar surface 380 for facile release from slot 350.

As assembly 300 is pulled proximally from the state seen in FIG. 19A to the state seen in FIG. 19B, arms 308 and 310 are compressed inwardly. Each arm 308 and 310 comprises a latching foot, respectively designated 382 and 384, which engages and grips a distal annular surface 386 of central body 326. In this manner, fore-part 302 is releasibly adjoined to aft-part 304 while assembly 300 is pulled forward to a cocked position. In its most proximal position, arms 308 and 310 are outwardly biased into slots 354 and 356, respectively. In this position, feet 382 and 384 catch against edges 360 and 362 to form a permanent latch thereat. Note that outward biasing of arms 308 and 310 release the grasp of feet 382 and 384 against surface 386, thereby releasing the grip of aft-part 304 by fore-part 302.

When the grip of aft-part 304 is so released, needle 140 is relieved of proximal containment in tube 80 when aft-part 304 is triggered to a released state to be distally displaced by contraction of tube 180. Referring once more to FIG. 18C, aft-part 304 is released from a cocked state by depressing area 148 in the direction of arrow 388. Such depression forces wing 328 inward until the part of wing 328 along line 374 and latch point 372 clears edge 364. Contraction of elastic tube 180 retracts aft-part 304 and needle 140, to which the aft-part is securely affixed, into the distal section of tube 80 seen in FIG. 18A. Fore-part 302 remains proximal in tube 80 to effectively plug the hole formed by removal of hub 282 and collar 114. Note that fore-part 302 comprises a threaded hub 132', similar to hub 132.

Reference is now made to FIG. 21 where an exploded view of parts which are comprised in the alternate embodiment seen in FIGS. 16–20 is seen. The alternate embodiment parts comprise barrel section 20', tube 180, needle hub assembly 300 and needle containment section 30.

Assembly of the parts seen in FIG. 21 into a complete needle retracting device 10', which is functionally equivalent to device 10, involves the following steps:

1. Affixing tube 180 to hub 332;
2. Biasing wings 308, 310 and 328 inwardly and sliding assembly into cylinder 340 for engagement with slots 348, 350 and 352, respectively;
3. Affixing tube 180 to hub 262. Note that access to hub 262 is provided through slot 346;
4. Laterally displacing section 30 such that the threaded connecting segment 274 of needle cover 120 engages hub 132';
5. Rotating section 30 to affix hub 132' to needle cover 120 (assembly 300 is restrained from rotating because wing 330 is disposed in slot 346 both during assembly and cocking procedures;
6. Affixing section 30 to section 20', preferably by application of adhesives or by ultrasonic welding to form a hermetically sealed package about needle 140.

Figure 22:
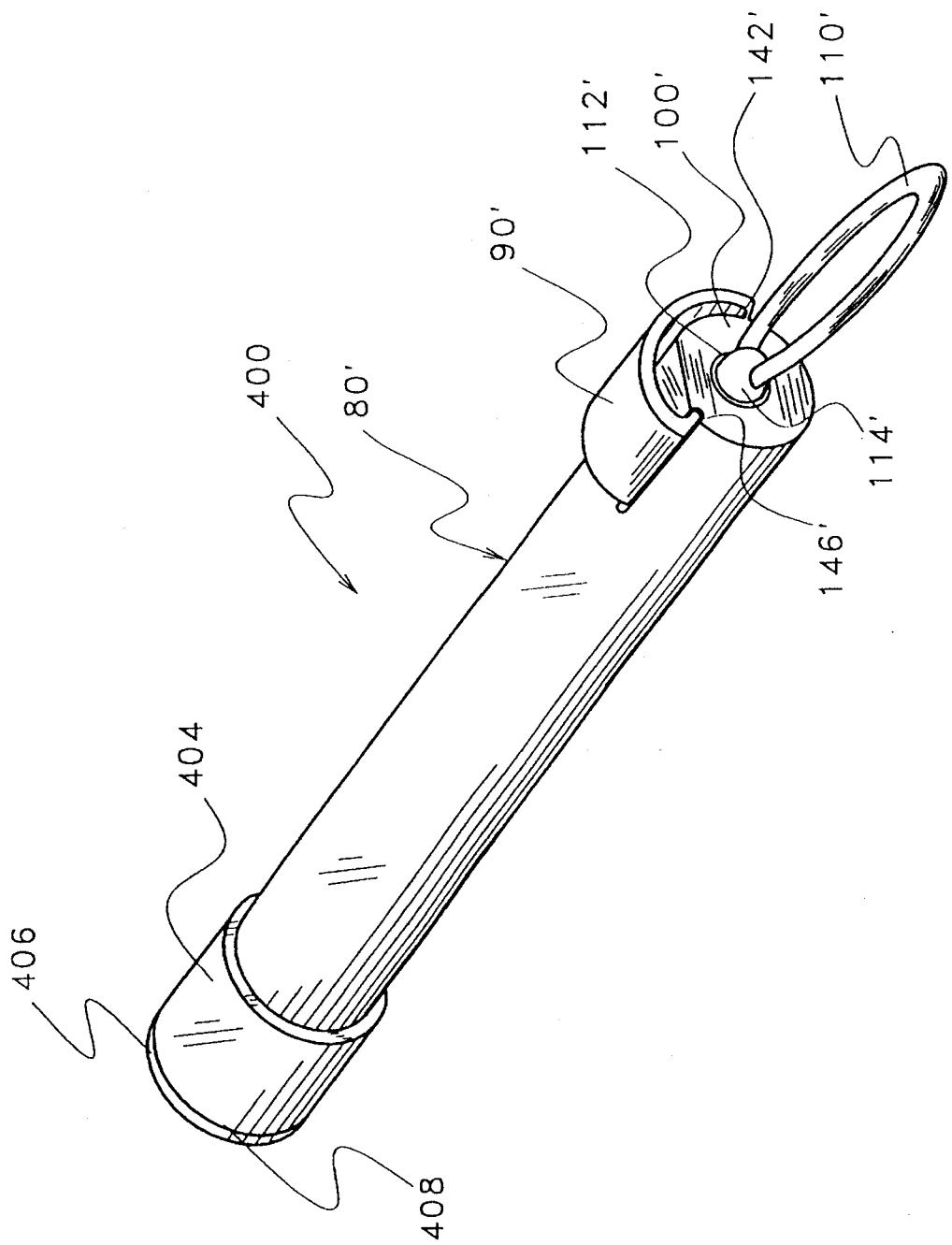
FIG. 22 is perspective of an alternate embodiment of the invention showing a totally enclosed IV catheter insertion assembly.
Figure 23:
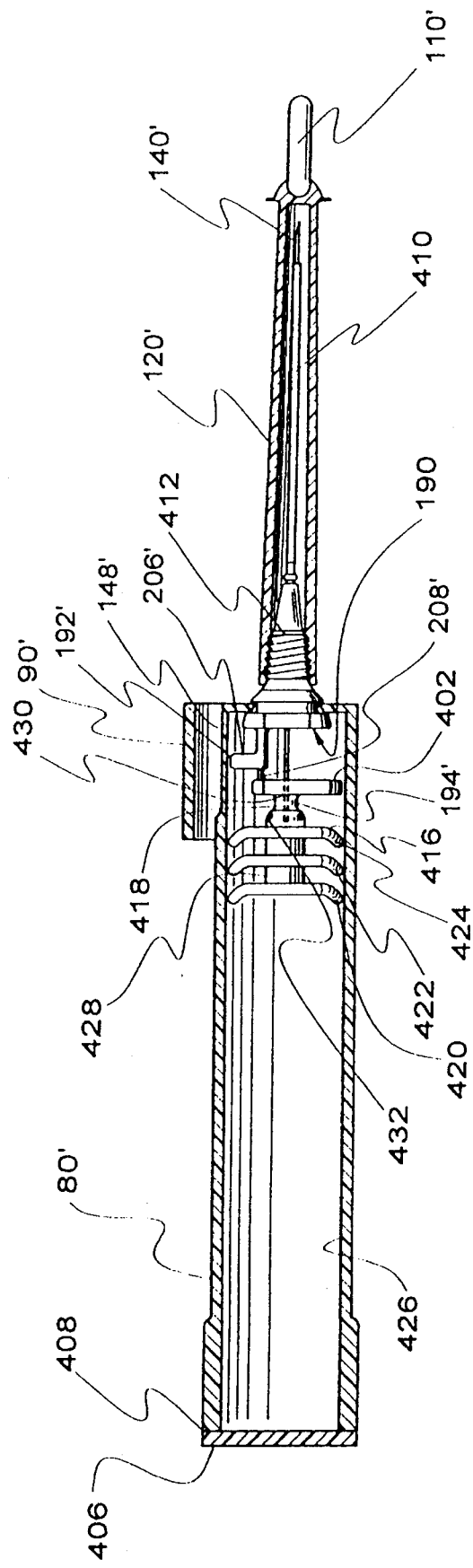
FIG. 23 is a longitudinal section of the assembly seen in FIG. 22.

Reference is now made to FIGS. 22 and 23 where a catheter insertion apparatus 400, another embodiment of the invention, is seen. A closed, transport compatible package of apparatus 400 is seen in FIG. 22. Exteriorly, apparatus is seen to comprise a pull ring 110' affixed to and integral with a front face plate 100', which is similar to face plate 100. Face plate 100' is integral with a tube 80' which is also similar in form and function to tube 80. Face plate 100' also comprises an annular frangible segment 112' which permits ring 110' and a collar portion 114' of plate 100' to be frangibly separated from plate 100' when pulling a needle assembly proximally from tube 80' for use.

Tube 80' comprises a flap 90' which, similar in form and function to flap 90, is releasibly affixed to a groove 146' and on an opposite end attached by a living hinge 142' to tube 80'. Tube 80' is elongated to fully contain a needle 140' used in catheter insertion and a needle withdrawal mechanism 402, as seen in FIG. 23.

At its distal end, tube 80' comprises an annular raised section 404 which acts as a handle during the needle pulling procedure. Further apparatus 400 comprises a distal plate 406 which is securely affixed at the distal end 408 of tube 80' to enclose and hermetically seal needle 140' and withdrawal mechanism 402 inside tube 80'.

Withdrawal mechanism 402 comprises a needle/hub part 160' which is similar to part 160 in form and function. Basic ways in which part 160' departs from the form of part 160 is found at the proximal and distal segments of part 160'. Proximally, part 160' comprises a secondary connection 412 for a transcutaneous catheter 410.

Such catheters and catheter connections are well known in the transcutaneous catheter art. Also needles used with transcutaneous catheters are readily available. A common source is Becton Dickenson Corporation of Franklin Lakes, N.J. 07417-1883. A current source for such catheters is Abbot Hospitals, Inc., North Chicago, Ill. 60064. The material from which tube 80' and plate 406 is made is similar to materials prescribed for tube 80.

Distally part 160' comprises a connection 414 whereby a return energy storing component 416 is affixed to a hub 418 portion of part 160'. As seen in FIG. 23, part 160' comprises catheter needle 140', a fore part 190' proximal to the sharp end of needle 140', a central part 192', and an aft part 194'. With the exceptions of proximal and distal connections of mechanism 402, parts 190', 192' and 194' are substantially the same in form and function to parts 190, 192 and 194. A bridge part 208' and upwardly extending part 206', each being respectively similar in form and function to bridge 208 and part 206, are similarly inwardly disposed for compressible access via a depressible area 148' of tube 80'.

Markedly different, although within the scope of the invention is return energy storing component 416. Component 416 comprises a plurality of piston head parts 420, 422 and 424 which communicate with an inner wall 426 of tube 80' to effectively pull and retain a vacuum as mechanism is moved proximally. The vacuum contained in tube 80' provides the force which retracts needle 140' when bridge 208' is frangibly broken. To provide an adequate retraction force, parts 420, 422 and 424 must create a differential force of at least four pounds to overcome forces of stiction in both the needle and other retracting mechanisms. For apparatus 400 to have substantially universal use, a minimum atmospheric pressure of ten pounds per square inch is assumed. For a minimum pressure of four pounds realized from an atmospheric pressure of ten pounds per square inch, each part 420, 422 and 424 must have a minimum area of four tenths of a square inch. As parts 420, 422 and 424 are essentially circular planes, their diameter must be a minimum of 0.36 inches (0.9 centimeters).

Parts 420, 422 and 424 are securely affixed to a medially disposed piston hub 428 which is in turn likewise affixed to mechanism 416 via aft part 194'. As indicated by dashed lines 430, needle 140' communicates with hub 428 via part 194. Hub 428 is a hollow vessel which is completely sealed, except for a gas communicating plug 432 disposed proximal from part 424.

Plug 432 is made from a hydrophobic material which is permissive to passage of gas (air), but retards flow of water based liquids (such as blood). The preferred material is Goretex, a material available from W. L. Gore Company, Arizona, USA. Plug 432 is securely affixed hub 428 to provide a pathway for gas to relieve pressure as blood is communicated into hub 428 through needle 140'.

Hub 428 is made from either translucent or transparent materials through which blood may be seen. Thus, by providing the pathway from needle 140' into hub 428 and permitting air to escape from hub 428 as influent blood arrives, hub 428 provides a visually determinable blood "flash" which is commonly used to ascertain entry of needle 140' into a blood vessel.

To use apparatus 400, ring 110' and collar 114' are frangibly separated from plate 100'. Needle cover 120', needle 140' and catheter 410 are pulled from tube 80' until mechanism 402 is firmly attached to plate 100'. By this action a vacuum is created in the portion of tube 80' which is distal to part 420. Cover 120' is removed and needle 140' and catheter 410 are transcutaneously inserted into a patient following good medical practices. When needle 140' enters a blood vessel, blood is communicated to hub 428 through which a blood "flash" communicates to the attending technician that the vessel has been entered. At this point, flap 90' is lifted to provide access to area 148'. A portion of area 148' is depressed to frangibly break bridge 208' which releases the aft portion 194' of mechanism 402 to be retracted by force stored via parts 420, 422 and 424 in cooperation with tube 80'. Needle 140' is thereby withdrawn. Note that the only pathway through blood may be communicated upon withdrawal of needle 140' is into tube 80'. This limitation upon needle withdrawal is a definite advantage over non-self-retracting needle systems currently in use. Under appropriately controlled conditions, catheter 410 is removed for attachment of other medical devices.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. Apparatus for transporting and using and then safely withdrawing a medical needle directly from a patient into a container after use, said apparatus comprising:

the container comprising a catch for a medical needle latch, an exit and reentry end for access to the medical needle, an opposite end juxtaposed the exit and reentry end and a means for releasing the latch from the catch;

a needle cover frangibly affixed to said container at the exit and reentry end before use, the needle cover in combination with the container forming a protective barrier for contents of the cover and container;

a medical needle assembly disposed within said cover and container, the assembly comprising:

a medical needle comprising a sharpened point for percutaneous entry into a patient and a pathway for flow of medical fluids;

connector hub means comprising:

means for releasably affixing the medical needle assembly to the cover such that when the cover is pulled from the container the medical needle is extended outwardly from the container for use;

at least one hub which is securely affixed to the medical needle; and at least one latch which is securely but releasably affixed by the catch to a predetermined position within the container when the medical needle is extended for use;

an elastic tube which is securely affixed on a first end to the connector hub means to provide a continuation of said pathway through the elastic tube and which is securely affixed on a second end to a part on the opposite end of the container wherethrough the pathway is continued for connection to a medical fluid containment vessel, the elastic tube being elongated to store energy for needle retraction when the connector hub means and opposite end are moved apart thereby providing a retracting force which acts to return the needle to the container when the latch is released.

2. Apparatus according to claim 1 wherein the latch releasing means comprises a distortable portion of the container.

3. Apparatus according to claim 1 wherein the hub means comprises two hub parts, a first hub which is securely affixed to the medical needle and a second hub which is releasably affixed to the first hub part, the second hub comprising a latch which secures and permanently affixes the second hub at the exit and entry end of the container when the needle is extended and which remains at the exit and entry end of the container when the needle is retracted to assure that the medical needle can only be extended and retracted once.

4. Apparatus according to claim 1 wherein the elastic tube is made from material selected from a group of materials comprising medical grade latex and silicone rubber.

5. Apparatus according to claim 1 wherein the container comprises a means for communicating with a vacuum tube to which the pathway continues.

6. Apparatus according to claim 5 wherein the vacuum tube is a Vacutainer®.

7. Apparatus according to claim 1 further comprising a one way valve in the pathway for the purpose of restricting regurgitant flow through the needle.

8. Apparatus according to claim 1 wherein the means further comprise a means for obstructing flow through the needle while the needle is being retracted.

9. A method for using and disposing of a medical needle comprising the following steps:

provautomatic a medical transport container having a medical needle cover and medical needle, the medical needle being at least partially disposed within the container for antiseptic protection before use, the container comprising a communicating passage to a vessel for medical fluids which is disposed external to the container and an elastic tube securely interposed between the passage to the vessel and the medical needle to provide a fluid pathway therebetween;

extending the medical needle cover and thereby the medical needle outwardly from the container to a position whereat the needle is securely, but releasably latched and disposed ready for use;

concurrently and as a result of extending the medical needle elastically elongating the elastic tube thereby storing in the stretched tube energy to return the needle to the container while preserving the pathway from the needle to the vessel communicating passage;

following a medical procedure to use the medical needle;

retracting the needle into the container by releasing the latch.

10. A method according to claim 9 wherein the retracting step comprises leaving an obstruction in the pathway of the retracting needle to assure the medical needle can be used but once.

11. A method according to claim 9 wherein the following step comprises causing a medical fluid to usefully flow through the tube.

12. A method according to claim 9 wherein the retracting step comprises obstructing flow through the needle.

13. A method according to claim 9 wherein the following step comprises drawing fluid from a patient and restricting fluid flow through the needle to only fluid flow from the patient.

14. A method according to claim 9 wherein the tube providing step comprises providing an elastic tube made from a group of materials comprising medical grade latex and silicone rubber.

15. A method according to claim 9 wherein the releasing step comprises disengaging the latch while the needle resides within a patient.

16. A method for making a safe medical needle transport, medical needle use and sharp needle trap apparatus comprising the following steps:

providing an elongated tubular container comprising an internally disposed catch, an exit and entry end through which a medical needle can be extended for use and retracted after use, and means for communicating fluid to a vessel external to the container;

providing a medical needle cover and a medical needle having a hub and a latch which selectively can be aligned to be securely but releasably affixed to the catch when the needle is extended for use;

providing an elastic tube which is compatible with medical fluids which flow therethrough;

shrouding the medical needle inside the needle cover;

affixing one end of the elastic tube to the fluid communicating means;

connecting the other end of the elastic tube to the hub, thereby constructing a continuous fluid pathway from the medical needle to the fluid communicating means and establishing a means for storing energy when the needle is extended through the exit and reentry end of the container, the stored energy to be used afterward to retract the medical needle after use; disposing the elastic tube and medical needle inside the container with the needle cover at least partially disposed within the container.

17. A method according to claim 16 wherein the elastic tube providing step comprises providing tube made of material selected from a group of materials comprising medical grade latex and silicone rubber.

18. A method according to claim 16 wherein the shrouding step comprises frangibly affixing the cover to the container at the exit and entry end to form a barrier to protect the medical needle during transport and prior to use.

19. Apparatus for transporting a sharp pointed medical needle before use at least partially enclosed within a container and having the needle and its point protected by a cover, for baring the needle to perform a medical procedure and for safely retracting the needle into the container for safe disposal after use, said apparatus comprising:

the container;

the cover which in cooperation with the container protects the needle and its point prior to use and which is removable from covering the needle to permit use of the needle;

the medical needle through which medical fluids flow during the medical procedure, the medical needle being first transported in the container and cover, extended from the container for use and later retracted back into the container where the sharp point is protectively enclosed;

an elastic tube which is used to provide passage for medical fluids which flow through the needle and which is used to provide a force from energy stored when the needle is extended to retract the needle into the container.

20. Apparatus for transporting and using and then withdrawing a medical needle to a safe container after use, said apparatus comprising:

a container comprising:

a needle exit and reentry end disposed proximal to a site of needle entry into a patient, said end comprising means for providing a sterile barrier prior to extending the needle through the exit and reentry end;

a portion proximal to the exit and reentry end being physically distortable without breaking said container;

an opposite end associated with blood delivery to a storage vessel for later use;

a frangibly attached needle cover, initially, at least partially, disposed within said container but having a closed, but separable attachment at said needle exit and reentry end such that the cover is physically detachable from the rest of the housing at the needle exit and reentry end and is thereby provided with an exit path through the exit and reentry end;

at least one surface segment comprising a catch for a latch;

a medical needle assembly comprising:

a medical needle initially disposed within the needle cover and having a sharpened end disposed toward the needle exit and reentry end;

cover attachment hub means disposed about said medical needle and separably attachable to and detachable from the needle cover, said cover attachment hub being slideably affixed to said needle during transport and before and during blood withdrawal;

said cover attachment hub means further comprising a latch which, prior to blood withdrawal, is positioned to lock, by interaction with said at least one surface segment, said needle assembly at a predetermined position relative to said exit and reentry end whereat the needle extends outward from said housing and is thereby positioned for use;

a needle release assembly firmly affixed to said medical needle at least an end of the assembly distal from the opposite end, said release assembly comprising:

a releasable attachment to said cover attachment hub;

an attachment release apparatus disposed in close communication with an internal surface of said container such that the release apparatus is actuated after the needle is extended by manual distortion of the physically distortable portion of said container;

means for affixing said needle assembly to a linear motion force storage apparatus which derives return energy for needle retraction from needle extension through the needle exit and reentry end;

a blood containment and delivery pathway from the needle to the opposite end;

means for delivering blood from the containment pathway to the storage vessel.

21. A method for storing, before use, a medical needle as part of a medical needle retraction device which does not deteriorate over time due to containment of parts stressed during storage, then using and disposing of a medical needle comprising the following steps:

providing a medical transport container having a medical needle cover and a medical needle assembly, comprising the medical needle, at least partially disposed within the container for antiseptic protection before use, the container comprising a communicating passage to a vessel for medical fluids which is disposed external to the container and an elastic tube securely interposed between the passage to the vessel and the medical needle to provide a fluid pathway therebetween;

the container further comprising a catch for a latch and the medical needle assembly comprising the latch which is maintained in a non-stressed state prior to use;

extending the medical cover and therefore the medical needle outwardly from the container to a position whereat the needle is securely, but releasibly latched and disposed ready for use, the latch moving from a non-stressed state to a stressed state only while the medical needle is moved outwardly an until the latch is secured;

concurrently and as a result of extending the medical needle elastically elongating the elastic tube thereby storing in the stretched tube energy to return the needle to the container while preserving the pathway from the needle to the vessel communicating passage, the elastic tube being stressed by the elongation only while the needle is extended;

following a medical procedure to use the medical needle;

retracting the needle into the container by momentarily restressing the latch to accomplish its release form the catch.

* * * * *